United States Patent [19]

Cheng et al.

[11] Patent Number: 5,728,684

[45] Date of Patent: Mar. 17, 1998

[54] DETERMINATION OF PRODRUGS METABOLIZABLE BY THE LIVER AND THERAPEUTIC USE THEREOF

[75] Inventors: Yung-Chi Cheng, Woodbridge; Chien-Neng Chang, New Haven, both of Conn.

[73] Assignee: Yale University, New Haven, Conn.

[21] Appl. No.: 146,164

[22] PCT Filed: May 15, 1992

[86] PCT No.: PCT/US92/04142

§ 371 Date: Apr. 19, 1994

§ 102(e) Date: Apr. 19, 1994

Related U.S. Application Data

[63] Continuation-in-part of Ser. No. 701,462, May 15, 1991, abandoned, and Ser. No. 829,474, Feb. 3, 1992, abandoned, which is a continuation-in-part of Ser. No. 701,462.

[51] Int. Cl.$^6$ .................................................. A01N 43/04
[52] U.S. Cl. .......................... 514/50; 514/45; 514/49; 514/256; 514/257; 514/261; 514/274; 514/300; 435/25; 536/27.13; 536/27.14; 536/27.21; 536/27.6; 536/28.1; 536/28.2; 536/28.5; 536/28.53; 544/242; 544/245; 544/264; 544/317
[58] Field of Search .................... 536/27.13, 27.14, 536/27.21, 27.6, 28.1, 28.2, 28.5, 28.53; 435/25; 514/45, 49, 50, 256, 257, 261, 274, 300; 544/242, 245, 264, 317

[56] References Cited

U.S. PATENT DOCUMENTS

| | | | |
|---|---|---|---|
| 4,468,384 | 8/1984 | Bardos et al. | 514/49 |
| 4,782,142 | 11/1988 | Bardos et al. | 536/26.8 |
| 4,895,937 | 1/1990 | Bardos et al. | 536/28.1 |
| 4,942,226 | 7/1990 | Saari | 536/28.55 |

FOREIGN PATENT DOCUMENTS

| | | |
|---|---|---|
| 0175004 | 3/1986 | European Pat. Off. |
| 0287215 | 10/1988 | European Pat. Off. |
| 92/01452 | 2/1992 | WIPO |
| 92/04901 | 4/1992 | WIPO |

OTHER PUBLICATIONS

Weller et la., The Lancet, vol. 1, "Acyclovir Inhibits Hepatitis B virus Replication In Man", pp. 273 (30 Jan. 1982).

Vere Hodge, R.A., et al., "Selection of an Oral Prodrug (BRL 42810; Famciclovir) for the Antiherpesvirus Agent BRL 39123 [9-(4-Hydroxy-3-Hydroxymethylbut-1-yl)Guanine; Penciclovir]", *Antimicrobial Agents and Chemotherapy*, vol. 33, No. 10, pp. 1765-1773, Oct. 1989.

Petty, B.G., et al., "Pharmacokinetics and Tolerance of Desciclovir, a Prodrug of Acyclovir, in Healthy Human Volunteers", *Antimicrobial Agents and Chemotherapy*, vol.31, No. 9, pp. 1317-1322, Sep. 1987.

Daniels, S., et al., "Drug Interaction Studies and Safety of Famciclovir in Healthy Volunteers: A Review", *Antiviral Chemistry & Chemotherapy*, vol. 4, Suppl. 1, pp. 57-64, 1993.

Chang, C.N. et al., "Demonstration of a Unique Liver Enzyme Activity Which Converts 5-Iodo-2-Pyrimidinone-2'Deoxynucleoside to 5-Iodo-Deoxyuridine and its Implications on Hepatotropic Drug Design", *Proceedings of American Association for Cancer Research* 32:406 A2415 (Mar. 1991).

Lewandowski, G.A. et al., "Anti-Herpes Simplex Virus Activity of 5-Substituted 2-Pyrimidinone Nucleosides", *Antimicrobial Agents and Chemotherapy* 33/3:340-344 (1989).

Doctoral Dissertation of Gail A. Lewandrowski entitled: The Biological Activity and Mechanism of Action of of the Anti-Herpes Simplex Virus Compound 5-Iodo 2-Pyrimidinone 2-Deoxyribocnulease.

Krenitsky, et al., *Proc. Natl. Acad. Sci. USA*, vol. 81, pp. 3209-3213, 1984.

Doong et al., *Proc. Natl. Acad. Sci. USA*, vol. 88: pp. 8495-8499.

Iigo et al., *JPN. J. Cancer Research*, vol. 81: pp. 431-435, Apr. 1990.

Yamashita et al., *Cancer* vol. 64: pp. 2437-2444, 1989.

Efange, S.M.N., et al., "Synthesis and Biological Activities of 2-Pyrimidinone Nucleosides. 2. 5-Halo-2-pyrimidinone 2'-Deoxyribunucleosides", *J. Med. Chem.*, vol. 28, No. 7, pp. 904-910, 1985.

Lewandowski, G.A., et al., "Mechanism and Mode of action of 5-Iodo-2-pyrimidinone 2'-Deoxyribunucleoside, a Potent Anti-Herpes Simplex Virus Compound, in Herpes Simplex Virus-Infected Cells", *Mol. Pharmacol.*, vol. 39, No. 1, pp. 27-33, Jan. 1991.

Shih, H-C., "Studies in the Design of New Antitumor and Antiviral . . . As Potential Antiviral Agents", *Database Dissertation Abstracts Host: CD Plus*, and *Dissertation Abstracts International*, vol. 43, No. 01, Section 8, p. 0087.

Driscoll, J.S., et al., "Antitumor Properties of 2(1H)-Pyrimidinone Riboside (Zebularine) and Its Fluorinated Analogues", *J. Med. Chem.*, vol. 34, No. 11, pp. 3280-3284, Nov. 1991.

Kinsella, T.J., et al., "An *in Vivo* Comparison of Oral . . . Colon Cancer Xenograft, HCT-116", *Cancer Research*, vol. 54, No. 10, pp. 2695-2700, 15 May 1994.

(List continued on next page.)

*Primary Examiner*—James O. Wilson
*Attorney, Agent, or Firm*—Browdy and Neimark

[57] ABSTRACT

A method of ascertaining if a prodrug is useful for treating a disease is disclosed. The prodrug is acceptable if it is metabolized in liver cells by aldehyde oxidase to produce an active drug or metabolite. Prodrugs are shown equally effective in treating diseases as the active drug itself with many benefits and without as many associated side effects. Methods for treating cancers with 5-iodo-2-pyrimidinone-deoxyribose and 5-fluoro-2-pyrimidinone are also described.

23 Claims, 8 Drawing Sheets

OTHER PUBLICATIONS

Chang, C-N., et al., "Conversion of 5–Iodo–2–Pyrimidinone–2' Deoxyribose to 5–Iodo–Deoxyuridine by Aldehye Oxidase", *Biochem. Pharmacol.*, vol. 43, No. 10, pp. 2269–2273, 28 May 1992.

Kunugi, K.A., et al., "Comparison of Iododeoxyuridine and ... tissues and HCT–116 xenografs", *Proc. Annu. Meet. Am. Assoc. Cancer Res.*, vol. 34, p. 413, Abstract No. 2466, Mar. 1993.

Guo, X., et al., "Development of a prodrug of 5–Fluorouracil", *Proc. Annu. Meet. Am. Assoc. Cancer Res.*, vol. 34, p. 416, Abstract No. 2483, Mar. 1993.

Johns, et al., "Enzymic hydroxylation of 5–fluoropyrimidine by aldehyde oxidase and xanthine oxidase", *Biochem. Pharmacol.*, vol. 15, No. 3, pp. 400–403, 1966.

Johns, D.G., "Human liver aldehyde oxidase: Differential inhibition of oxidation of charged and uncharged substrates", *J. Clin. Inv.*, vol. 46, No. 9, pp. 1492–1505, 1967.

Sartorelli, et al., "The antineoplastic and biochemical affects of some 5–fluoropyrimidines", *Cancer Res.*, vol. 27, No. 11, Pt. 1, pp. 2201–2206, 1967.

Oftebro, et al., "5–Fluoropyrimidin–2–one, a new metaphase arresting agent", *Biochem. Pharmacol.*, vol. 21, pp. 2451–2456, 1972.

Miwa et al., "Comparative Studies on the Antitumor and Immunosuppressive Effects of the New Fluorouracil Derivative $N^4$–Trimethoxybenzoyl–5'–deoxy=5–fluorocytidine and Its Parent Drug 5'–Deoxy–fluorouridine", *Chem. Pharm. Bull.*, 38(4):998–1003 (1990).

Ninomiya, Y. et al., "Comparative Antitumor Activity and Intestinal Toxicity of 5'–Deoxy–5–fluorouridine and Its Prodrug Trimethoxybenzoyl–5'–deoxy–5–fluorocytidine", *Jpn. J. Cancer Res.*, 81:188–195 (Feb. 1990).

Nio, Y. et al., "A Comparative Study of the Antitumor Activities of 5'–Deoxy–5–fluorouridine and its Prodrug Trimethoxy benzoyl–5'–deoxy–5–fluorocytidine (Ro09–1390) on Human Digestive Organ Cancer Xenograft Lines Transplanted into Nude Mice", *Anti–Cancer Drugs*, 3:389–383 (1992).

Brodie et al., "Detoxication of Drugs and Other Foreign Compounds by Liver Microsomes", *Science*, 121: 603–604 (Apr. 1955).

Sepulveda et al., "Development of a Transgenic Mous System for the Analysis of Stages in Liver Carcinogenesis Using Tissue–specific Expression of SV40 Large T–Antigen Controlled by Regulatory Elements of the Human $\alpha$–1–Antitrypsin Gene", *Cancer Research*, 49:6108–6117 (1989).

Felsted, et al., "Purification and Properties of the Aldehyde Oxidase from Hog and Rabbit Livers", *The Journal of Biological Chemistry*, 248(7):2580–2587 (1973).

Deme, et al., "The Thiol Groups of Rat Liver Cystathionase: Influence of Pyridoxal Phosphate, L–Homoserine and L–Alanine on the Effect of p–Chloromercuribenzoate and 5,5'–Dithiobis–(2–nitrobenzoate) on the Enzyme" *Eur. J. Biochem.*, 20:269–275 (1971).

Stanulovic et al., "Metabolic Origins of the Pyridones of N'–Methylnicotinamide in Man and Rat", *Archives of Biochemistry and Biophysics* 145:35–42 (1971).

Stanulovic et al., "Aldehyde Oxidase: Catalysis of the Oxidation of N'–Methynicotinamide and Pyridoxal", *Archives of Biochemistry and Biophysics* 145:27–35 (1971).

Speth et al., "Selective Incoroporaton of Iodedeoxyuridine into DNA of Hepatic Metastases versus Normal Human Liver", *Clin. Pharmacol. Ther.* 44(4):369–375 (1988).

Remick et al., "Phase I Trial of Hepatic Artery INfusion of 5–Iodo–2'–deoxyuridine and 5–Fluorouracil in Patients with Advanced Hepatic Malignancy: Biochemically Based Combination Chemotherapy", *Cancer Research* 49:6437–6442 (1989).

Kaufman et al., "Use of 5–Iodo–2'–deoxyuridine (IDU) in Treatment of Herpes Simplex Keratitis", *Archs. Ophthalmol.* 68:235–239 (1962).

Rajagopalan et al., "Hepatic Aldehyde Axidase: Purification and Properties", *The Journal of Biological Chemistry* 237(3):922–928 (1962).

Rajagopalan et al., "Hepatic Aldehyde Oxidase: Differential Inhibition of Electron Transfer to Various Electron Acceptors", *The Journal of Biological Chemistry* 239(6):2022–2035 (1964).

Kato et al., "Alcohol Oxzidases of *Kloeckera* sp. and *Hansenula polymorpha*", *Eur. J. Biochem.* 64:341–350 (1976).

George et al., "Identification of $\alpha$–Ketobutyrate as the Prosthetic Group of Urocanase from *Pseudomonas putida*", *The Journal of Biological Chemistry* 245(3):528–537 (1970).

Barber et al., "Properties of the Prosthetic Groups of Rabbit Liver Aldehyde Oxidase: A Comparison of Molybdenum Hydroxylase Enzymes", *Biochemistry* 21:3561–3568 (1982).

Keul et al., "Identification of the Prosthetic Group of Urocanase", *The Journal of Biological Chemistry* 254(3):843–851 (1979).

Weidig et al., "Evidence for the Site Equivalence in the Reaction Mechanism of Horse Liver Alcohol Dehydrogenase with Aromatic Substrates at Alkaline pH", *Biochemistry* 16(13):2916–2922 (1977).

Proc. Natl. Acad. Sci. USA, vol. 81, issued May 1984, Krenitsky et al., "6–Deoxyaclovir: A Xanthine Oxidase–activated Prodrug of Acyclovir", pp. 3209–3213.

Japan J. Cancer Res., vol. 81, issued Apr. 1990, Iigo et al., "Optimal Treatment Regimens for 5'–Deoxy–5–flourouridine, with or without (E)–5–(2–Bromovinyl)–2/–deoxyridine against Various Tumors in Mice", pp. 531–435.

Cancer, vol. 64, issued 15 Dec. 1989, Yamashita et al., "Intraarterial Infusion of 5–Fluoro–2–Deoxyuridine–C8 Dissolved in a Lymphographic in Malignant Liver Tumors", pp. 2437–2444.

WEEKS AFTER BIRTH (TREATED ONCE A WEEK)

—▲— CONTROL   —△— FP TREATED
             100 mg/kg × 2/d

DETERMINATION OF PRODRUGS METABOLIZABLE BY THE LIVER AND THERAPEUTIC USE THEREOF

CROSS-REFERENCE TO RELATED APPLICATIONS

The present application is the U.S. national phase filing of PCT application no. PCT/US92/04142 filed May 15, 1992, now abandoned, which was a CIP of application Ser. No. 07/829,474, filed Feb. 3, 1992, now abandoned and application Ser. No. 07/701,462, filed May 15, 1991, now abandoned, the latter two applications both being entirely incorporated herein by reference. Said application Ser. No. 07/829,474 was a CIP of said application Ser. No. 07/701,462.

FIELD OF THE INVENTION

The present invention relates to prodrugs metabolizable by the liver, and more particularly relates to treating disease using a prodrug metabolizable by a liver enzyme(s) to an active drug. It also concerns a method of ascertaining if a prodrug is useful for treating a disease.

BACKGROUND OF THE INVENTION

Iododeoxyuridine (IUdR) was synthesized as an antineoplastic agent in 1959 by Prusoff (Prusoff, W. H., (1959), *Biochem. Biophys. Acta*, 32, 295–296), and was the first thymidine analog used clinically as an anti-herpes agent (Kaufman, H. E., Martola, E. L. and Dohlman, C., (1962), *Archs. Ophthalmol.*, 68, 235–239). The toxicities associated with IUdR when used systemically limited its clinical usage. IUdR was also recognized as a potential clinical radiosensitizer for cancer chemotherapy (Kinsella, T. J., Mitchell, J. B., Russo, A., Morstyn, G. and Glatstein, E., (1984), *J. Radiation Oncology Biol. Phys.*, 10, 1399–1406). The degree of radiosensitization is directly dependent on the amount of thymidine replacement in DNA by this analog (Speth, P. A. J., Kinsella, T. J. Chang, A. E. Klecker, R. W., Belanger, K. and Collins, J. M., (1988), *Clin. Pharmacol. Ther.* 44, 369–375). Intrahepatic infusion of IUdR followed by radiation for the treatment of tumor cells in liver has had some success (Remick, S. C., Benson III, A. B., Weese, J. L., Willson, J. K. V., Tutsch, K. D., Fischer, P. H. and Trump, D. L., (1989), *Cancer Res.* 49 6437–6442).

In an attempt to develop selective anti-herpes simplex virus (HSV) agents based on the broader spectrum of substrate specificity of thymidine kinase of the herpes simplex virus compared to the human thymidine kinase, 5-iodo-2-pyrimidinone-deoxyribose (IPdR)—which differs from IUdR by a double bonded oxygen at the 4-position of the base—was synthesized. IPdR was found to have potent activity against HSV-1 and HSV-2 in cell culture and against HSV-2 in mice (Lewandowski, G. A., Grill, S. P., Fisher, M. H., Dutschman, G. E., Efange, S. M., Bardos, T. J. and Cheng, Y. C., (1989), *Antimicrob. Agents Chemother.*, 33, 340–344). This agent was not toxic to uninfected cells, nor to mice when given orally at the dosage employed (Lewandowski, G. A., Grill, S. P., Fisher, M. H., Dutschman, G. E., Efange, S. M., Bardos, T. J. and Cheng, Y. C., (1989), *Antimicrob. Agents Chemother.*, 33, 340–344). Since IPdR and IUdR are structurally related, the possible conversion of IPdR to IUdR was examined. It was shown previously that IPdR could not be converted to IUdR by xanthine oxidase (Lewandowski, G. A., Grill, S. P., Fisher, M. H., Dutschman, G. E., Efange, S. M., Bardos, T. J. and Cheng, Y. C., (1989), *Antimicrob. Agents Chemother.*, 33, 340–344)

U.S. Pat. Nos. 4,895,937 discloses the nucleoside 1-(2-deoxy-β-D-ribofuranosyl)-5-(iodo)-2-pyrimidinone (IPdR) for use as an agent against herpes viruses, for example HSV-2. The entire content of U.S. Pat. No. 4,895,937 is incorporated by reference herein.

NOMENCLATURE

IUdR: iodo-deoxyuridine

FUdR: fluoro-deoxyuridine

IPdR: 5-iodo-2-pyrimidinone-deoxyribose;

HSV: herpes simplex virus;

HPLC: high performance liquid chromatography;

IU: iodo-uracil;

EPdR: 5-ethynyl-2-pyrimidinone-deoxyribose;

IP: 5-iodo-2-pyrimidinone;

BPdR: 5-bromo-2-pyrimidinone-deoxyribose;

MPdR: 5-methyl-2-pyrimidinone-deoxyribose;

EtPdR: 5-ethyl-2-pyrimidinone-deoxyribose;

BUdR: 5-bromo-deoxyuridine dR: deoxyribose

HBV: hepatitis B virus

FU: 5-fluoro uracil

FP: 5-fluoro-2-pyrimidinone ddI: dideoxyinosine ddG: dideoxyguanine

DHPG: ganciclovir (9-[(1,3-dihydroxy-2-propoxy)methyl]guanine)

ACV: (S)-N-[N-(5-amino-5-carboxy-1-oxopentyl)-L-cysteinyl]-D-valine

D4T: 2,3'-dideoxy-2',3'-didehydrothymidine

AZT: 3'-azido-3'-deoxythymidine

SUMMARY OF THE INVENTION

It is an object of the present invention to provide compositions for use as prodrugs which are metabolizable in the mammalian liver into a biologically active substance, particularly a biologically active substance which is intended to exert its biological effect in the liver or one which cannot be administered orally.

It is another object of the present invention to provide compositions comprising 5-substituted PdR analogs, particularly IPdR, for use as prodrugs which are metabolizable in the mammalian liver (especially the human liver) to form in situ the corresponding biologically active 5-substituted UdR compounds.

It is a further object of the present invention to use such 5-substituted PdR analogs for treatment of liver-associated diseases and particularly as a radiosensitizer for hepatocarcinoma.

It is still a further object of the present invention to provide compositions other than 5-substituted PdR analogs for use as prodrugs which are metabolizable in the mammalian liver into a biologically active substance, particularly a biologically active substance which is intended to exert its biological effect in the liver or one which cannot be administered orally.

It is yet a further object of the present invention to provide such compositions other than 5-substituted PdR analogs which are 5-substituted pyrimidinone analogs, particularly FP.

It is still another object of the present invention to provide such compositions other than 5-substituted PdR analogs which are prodrugs for the formation of biologically active nucleosides or nucleoside bases other than UdR and U, preferably analogs of guanosine, cytidine, inosine or thymine.

It is another object of the present invention to provide for improvements in the treatment of disease.

It is a further object of the present invention to provide a method of ascertaining if a prodrug is useful for treating a disease.

It is another object of the present invention to provide a method of determining whether a prodrug is metabolizable by a liver enzyme to a biologically active substance acting on any cell in the body.

It is another object of the present invention to provide a method of treating a disease using a prodrug.

It is yet another object of the present invention to provide a method for synthesizing a chemical compound using an aldehyde oxidase enzyme.

The above objects, as well as other objects, aims and advantages are satisfied by the present invention.

The present invention concerns a method of ascertaining if a prodrug is useful for treating a disease in, for example, a mammal, and preferably a human, comprising determining whether or not a non-toxic prodrug is metabolized in liver cells, in vitro, by the enzyme hepatic aldehyde oxidase, wherein if the prodrug is metabolized into an active drug or other useful metabolite, it is an effective prodrug for use in treating a disease. The determination and use of prodrugs effective against liver associated and neoplastic diseases are of particular interest.

The present invention is also directed to a method of treating a disease in an animal comprising administering to the animal, preferably a human, a pharmaceutically effective amount of a nontoxic nucleoside analog or nucleoside base analog, or a salt or ester thereof, either alone or in admixture with a pharmaceutically acceptable carrier, the analog prodrug being capable of being metabolized in liver cells by aldehyde oxidase into an active drug or other useful metabolite.

DETAILED DESCRIPTION OF THE INVENTION

Figure 1:
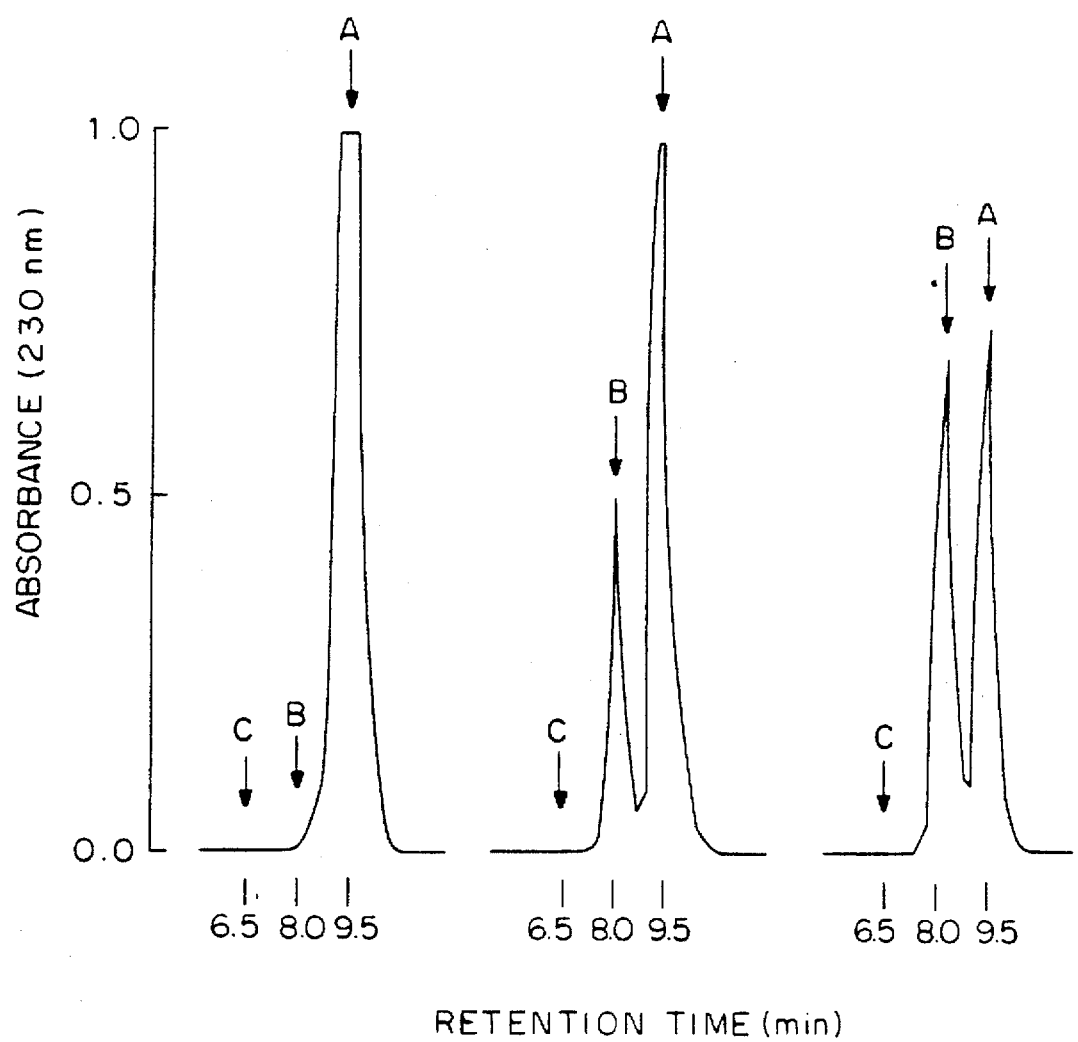
FIGS. 1A-1C depict HPLC profiles of the conversion of IPdR to IUdR by liver homogenate. IPdR was incubated with rat liver homogenate. For control reactions, a portion of the supernatant was boiled for 5 minutes to inactivate all enzymes before use. The assay condition was as described hereinafter except 60 µl of the 100,000 g×60 minute supernatant (equivalent to approximately 0.5 mg protein/ml) was used in a reaction volume of 1500 µl. Aliquots (300 µl) were removed at various time points (0 minutes (FIG. 1A), 15 minutes (FIG. 1B) and 30 minutes (FIG. 1C) during the incubation period at 37° C. The retention times were approximately 9.5 minutes for IPdR(A), 8.0 minutes for IUdR(B) and 6.5 minutes for IU(C) respectively.

The present invention is based on the discovery that prodrugs are activated by liver aldehyde oxidase in vitro and in vivo and become active drugs or metabolites to achieve a high selectivity and therapeutic index. The above is depicted by the following reaction scheme:

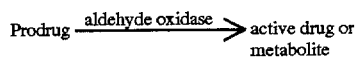

One reaction scheme of the above reaction scheme is as follows:

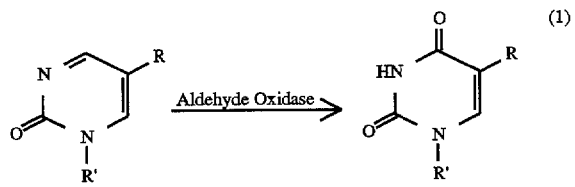

wherein

R is I, F, Br, Cl, H, —CH$_3$, —OR$^1$, —CF$_3$, NO$_2$, SR$^1$, —CH=CR$^2$R$^3$, —C≡CR$^2$ or —N=N$^+$—N$^-$, R$^1$ is an alkyl group from 1 to 5 carbon atoms, preferably having one carbon atom, R$^2$ and R$^3$, independently of each other, are hydrogen, a C$_1$-C$_5$-alkyl group or a halogen, and R' is hydrogen, a sugar residue such as ribose or deoxyribose, —CH$_2$—O—CH$_2$—CH$_2$OH, —CH$_2$—O—CH(CH$_2$OH), substituted or unsubstituted alkyl, aryl, cycloalkyl, cycloaryl or any other desired residue which is not of such size as to sterically hinder the action of the hepatic aldehyde oxidase. It has been shown that this residue does not interfere with the desired action of the hepatic aldehyde oxidase on the compound.

Other examples of reaction schemes are as follows:

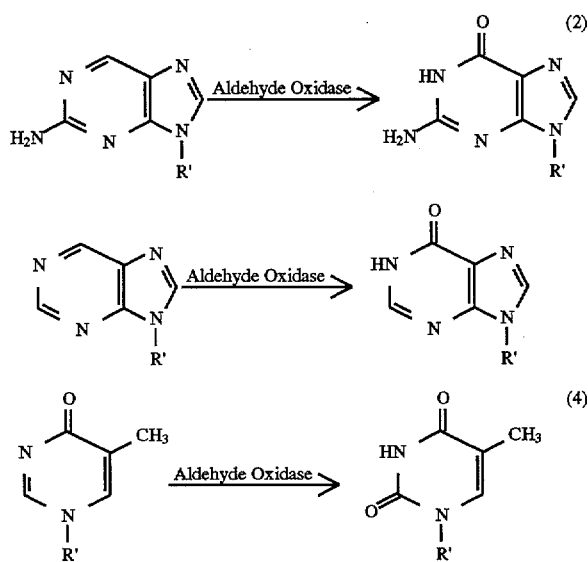

wherein

R' is as defined above.

The selection of prodrugs which can be tested or used in accordance with the present invention is limited only by the structure of the active drug being produced by the action of the hepatic aldehyde oxidase. Representative examples of useful prodrugs include nucleoside analogs and nucleoside base analogs. In this situation, the metabolized prodrug is converted into a product which is toxic to or is otherwise taken up so as to exert a desired biological effect (such as radiosensitization) only on proliferating cells (such as cancer cells) or to replicating virus, but is not toxic to or at least is less toxic to, or does not exert the same biological effect or less of the same biological effect on, nonproliferating cells.

Hepatic aldehyde oxidase is widespread among mammalian species. This enzyme catalyzes the oxidation of a variety of aliphatic and aromatic aldehydes as well as a number of non-aldehyde heterocyclic compounds such as $N^1$-methylnicotinamide, 4-amino-aminofolates and methotrexate and its analogs. The finding by the present inventors of the oxidation of 5-substituted pyrimidinones to their uracil or uridine counterparts by human or rat aldehyde oxidase has resulted in a complete new category of substrates acted upon by this enzyme. This discovery also allows the designing of drugs, metabolized in the liver, which can suppress and destroy cancer cells, viruses, parasites and other unwanted microbial pathogens.

To design prodrugs useful in the present invention, one needs only to select a bio-affecting compound, i.e., a compound exerting a desired biological effect, which compound has a keto group in its structure and which compound is desired to be formed in situ in the liver of an animal, particularly a mammal and most particularly a human. Any such bio-affecting compound having a keto group in its structure is a potential candidate for the present invention. Once such a bio-affecting compound is selected, a simple in vitro assay may be conducted to determine whether a corresponding prodrug will be oxidized to the bio-affecting compound in question by hepatic aldehyde oxidase.

The prodrug is formed by synthesizing a compound corresponding to the desired bio-affecting compound but the keto group thereof being in a reduced form. This potential prodrug is then subjected to an in vitro assay similar to that described in Examples 2 and 3 herein to determine whether it acts as a substrate for hepatic liver oxidase. If the prodrug is converted to the predetermined bio-affecting compound by the hepatic liver oxidase, then that prodrug may be considered a compound in accordance with the present invention and may be used in accordance with the present invention.

While 5-substituted PdR analogs are preferred and have been shown to convert to correspondingly substituted UdR compounds in vivo, it has also been established that the deoxyribose unit is not necessary for substrate specificity and that FP is also metabolizable to FU by hepatic aldehyde oxidase in vitro as well as in vivo. As most nucleosides and nucleoside bases include keto groups in their formula and many are structurally related to the structure of uracil, it is expected that bio-affecting compounds which are analogs of nucleosides and nucleoside bases are prime candidates for bio-affecting compounds for which prodrugs in accordance with the present invention can be designed, metabolizable by hepatic aldehyde oxidase into such compounds. Thus, in addition to uracil and uridine analogs, analogs of other nucleosides and nucleoside bases, such as cytidine, guanosine, 6-azauridine and 8-azaguanine analogs, may be used as the basis of the formation of prodrugs in accordance with the present invention. Examples of bio-affecting compounds in this category include ddG, DHPG, ACV, ddI, D4T and AZT.

Further examples of commercially available analogs of pyrimidines and purines which could serve as bio-affecting drugs for the design of corresponding prodrugs according to the present invention are listed in Tables I and II:

TABLE I

PYRIMIDINE ANALOGS

N'-Acetylcytidine
3'-O-Acetylthymidine
Allopurinol Riboside
4-Amino-5-Aminomethyl-2-Methyl-Pyrimidine
1-Aminobarbituric Acid
2-Amino-5-Bromo-6-Methyl Pyrimidinol
4-Amino-5-Carbethoxy-2-Ethyl-Mercaptopyrimidine
5-Amino-6-Carboxy-2,4-Dihydroxy-Pyrimidine
2-Amino-4-Chloro-6-Methyl-Pyrimidine
3'-Amino-3'-Deoxythymidine
5'-Amino-5'-Deoxythymidine
5'-Amino-2'-Deoxyuridine
5'-Amino-2',5'-Dideoxy-5-Iodocytidine
5'-Amino-2',5-Dideoxy-5-Iodouridine
4-Amino-2',6-Dihydroxy-5-NitrosoPyrimidine
2-Amino-4,6-Dihydroxypyrimidine
4-Amino-2,6-Dihydroxypyrimidine
5-Amino-2,4-Dihydroxypyrimidine
4-Amino-1,3-Dimethyl-2,6-Dioxy-5-Nitrosopyrimidine
2-Amino-4,6-Dimethylpyrimidine
4-Amino-2-Hydroxy-5-Hydroxy-Methylpyrimidine
4-Amino-6-Hydroxy-2-Mercapto-5-Nitrosopyrimidine
4-Amino-6-Hydroxy-2-Mercapto-Pyrimidine
2-Amino-4-Hydroxy-6-Methylpyrimidine
4-Amino-2-Hydroxy-5-Methylpyrimidine
2-Amino-4-Hydroxypyrimidine
4-Amino-2-Hydroxypyrimidine
4-Amino-6-Hydroxy-2-Thiopyrimidine
2-Amino-4-Methylpyrimidine
4-Aminoorotic Acid
4-Amino-2-Thiopyrimidine
6-Amino-2-Thiouracil
5-Amino-2,4,6-Trihydroxypyrimidine
4-Aminouracil
5-Aminouracil
6-Aminouracil
5-Aminouricine Amobarbital
2,3'-Anhydrothymidine
5-Azacytidine

TABLE I-continued

PYRIMIDINE ANALOGS

6-Azacytidine
5-Azacytosine
6-Azacytosine
5-Aza-2'-Deoxycytidine
6-Aza-2'-Deoxyuridine
6-Aza-2-Thiothymine
6-Azathymine
5-Azauracil
6-Azauracil Riboside
6-Azauridine
2'-Azido-2'-Deoxycytidine
3'-Azido-3'-Deoxythymidine
2'-Azido-2'-Deoxyuridine
Barbituric Acid
3'-O-Benzoylthymidine
5'-Benxoyluridine
5-Bromocytidine
5-Bromocytosine
5-Bromo-2'-Deoxycytidine
5-Bromo-2,3'-Dideoxyuridine
5-Bromo-2,4-Dihydroxypyrimidine
5-Bromo-2',3'-Isopropylidene-Uridine
5-Bromo-1-Methyluracil
5-Bromoorotic Acid
5-Bromouracil
5-Bromouridine
(E)-5-(2-Bromovinyl)Uridine
3-Butyluracil
5-Carbethoxycytosine
5-Carbethoxy-2,4-Dihydroxypyrimidine
5-Carbethoxy-2-Ethylmercapto-4-Hydroxpyrimidine
5-Carbethoxy-2-Thiouracil
5-Carbethoxyuracil
5-Carboxycytosine
5-Carboxy-2,4-Dihydroxypyrimidine
6-Carboxy-2,4-Dihydroxypyrimidine
5-Carboxy-2-Ethylmercapto-4-Hydroxypyrimidine
5-Carboxy-4-Hydroxy-2-Thiopyrimidine
Carboxymethyluracil
6-Carboxy-5-Nitro-2,4-Dioxypyrimidine
5-Carboxy-2-Thiouracil
5-Carboxyuracil
5-Chlorocytosine Arabinoside
5'-Chloro-5'-Deoxycytidine
2'-Chloro-2'-Deoxy-4-Thiouridine
2'-Chloro-2'-Deoxyuridine
5'-chlorodeoxyuridine
2-Chloro-4,5-Diaminopyrimidine
6-Chloro-2,4-Dimethoxypyrimidine
2-Chloropyrimidine
5-Chlorouracil
4,5-Diamino-2-Chloropyrimidine
4,5-Diamino-2,6-Dihydroxypyrimidine
2,5-Diamino-4,6-Dihydroxypyrimidine
4,6-Diamino-2-Ethylmercaptopyrimidine
4,6-Diamino-5-(Formylamino)-Pyrimidine
4,5-Diamino-6-Hydroxy-2-Mercaptopyrimidine
4,6-Diamino-2-Hydroxy-5-Nitrosopyrimidine
4,5-Diamino-6-Hydroxypyrimidine
2,4-Diamino-6-Hydroxypyrimidine
4,6-Diamino-2-Hydroxypyrimidine
4,6-Diamino-2-Methylmercaptopyrimidine
2,4-Diamino-6-Methyl-5-Nitropyrimidine
4,5-Diamino-6-Methyl-2-Thiopyrimidine
2,4-Diamino-5-Nitropyrimidine
4,5-Diaminopyrimidine
4,5-Diamino-2-Thiopyrimidine
4,5-Diamino-6-Thiopyrimidine
4,6-Diamino-2-Thiopyrimidine
5,6-Diaminouracil
5-Diazo-2'-Deoxyuridine
5-Diazouracil
4,6-Dichloro-5-Aminopyrimidine
2,4-Dichloro-6-Methylpyrimidine
2,4-Dichloropyrimidine
4,6-Dichloropyrimidine
2',3'-Dideoxycytidine

TABLE I-continued

PYRIMIDINE ANALOGS

2',3'-Dideoxyuridine
2,4-Diethoxypyrimidine
5,6-Dihydrodeoxyuridine
5,6-Dihydro-2,4-Dihydroxy-6-Methylpyrimidine
5,6-Dihydro-2,4-Dihydroxypyrimidine
Dihydro-6-Methyluracil
Dihydrothymidine
Dihydrothymine
Dihydrouracil
Dihydrouridine
2,6-Dihydroxy-4-Amino-5-Nitrosopyrimidine
2,6-Dihydroxy-4-Aminopyrimidine
2,4-Dihydroxy-6-Methyl-5-Nitropyrimidine
2,4-Dihydroxy-6-Methylpyrimidine
2,4-Dihydroxy-5-Nitropyrimidine
4,6-Dihydroxy-5-Nitroso-2-Thiopyrimidine
4,6-Dihydroxypyrimidine
2,4-Dihydroxypyrimidine-6-Methylsulfone
2,4-Dihydroxy-2-Thiopyrimidine
1,5-Dimethylcytosine
N,N-Dimethyl-2'-Deoxycytidine
1,3-Dimethyluracil
5,6-Dioxyuracil
2,4-Dithiopyrimidine
3,N'-Ethenocytidine
5-Ethyl-2'-Deoxyuridine
2-Ethymercapto-4,6-Diaminopyrimidine
5-Fluoro-2'-Deoxyuridine
Hexobarbital
5-Hydroxymethyl Cytosine
5-Hydroxymethyl-2'-Deoxyuridine
4-Hydroxy-6-Methyl-2-Thiopyrimidine
5-Hydroxymethyluridine
4-Hydroxypyrazolo-(3,4-d) Pyrimidine
2-Hydroxypyrimidine
4-Hydroxypyrimidine
4-Hydroxy-2-Thiopyrimidine
5-Hydroxyuracil
5-Hydroxyuridine
6-Hydroxyuridine
5-Iodocytidine
5-Iodocytosine
5-Iodo-2'-Deoxycytidine
5-Iodoorotic Acid
5-Iodouracil
5-Iodouridine
2',3'-O-Isopropylidenecytidine
2',3'-Isopropylideneuridine 5'-Triphosphate
5-Mercaptouracil
2'-O-Methylcytidine
3'-O-Methylcytidine
5-Methylcytidine
5-Methylcytosine
5-Methyl-2'-Deoxycytidine
5-Methyl-2-Thiocytosine
4-Methyl-2-Thiouracil
2-0-Methylthymidine
3-Methylthymidine
4-0-Methylthymidine
1-Methyluracil
3-Methyluracil
6-Methyluracil
2'-O-Methyluridine
3-Methyluridine
3'-0-Methyluridine
5-Methyluridine
5-Nitrobarbituric Acid
5-Nitro-6-Methyluracil
5-Nitroorotic Acid
5-Nitrosothiobarbituric Acid
5-Nitroso-2-4-6-Triaminopyrimidine
5-Nitrouracil
3'-Oxauracil
5-Propyl-2-Thiouracil
6-n-Propyl-2-Thiouracil
RIBAVIRIN ™
5-Sulfaminouracil

TABLE I-continued

PYRIMIDINE ANALOGS

2-Sulfanilamidopyrimidine
Tetrahydrouridine
2-Thio-6-Azauridine
2-Thio-5-Carboxyuracil
2-Thiocytidine
2-Thiocytosine
4-Thio-2'-Deoxyuridine
Thiomethyluracil
2-Thiopyrimidine
2-Thiouracil
5-Thiouracil
2-Thiouracil-5-Carboxylic Acid
4-Thiouridine
2,4,5-Triamino-6-Hydroxypyrimidine
4,5,6-Triamino-2-Hydroxypyrimidine
2,4,6-Triamino-5-Nitrosopyrimidine
2,4,6-Triaminopyrimidine
4,5,6-Triaminopyrimidine
2,4,6-Trichloropyrimidine
Trifluorothymidine
2,4,5-Trihydroxypyrimidine
Uramil ™

TABLE II

PURINE ANALOGS

3'-O-Acetyl-2'-Deoxycytidine
N'-Acetylguanine
2-Amino-6-Benzylmercaptopurine
2-Amino-6-Benzylthipurine
2-Amino-8-Bromo-6-Hydroxypurine
2-Amino-6(α-Carboxyethyl)-Mercaptopurine
2-Amino-6-Carboxymethyl-Mercaptopurine
2-Amino-6-Chloropurine
2-Amino-6-Chloropurine Riboside
6-Amino-2,8-Dihydroxypurine
8-Aminoguanosine
2-Amino-6-Mercaptopurine
6-Amino-2-Methylpurine
6-Amino-3-Methylpurine
2-Aminopurine
8-Azaxanthine
8-Azidoadenosine
6-Benzylaminopurine
6-Benzylaminopurine Riboside
1-Benzylinosine
8-Bromoadenine
8-Bromoadenosine
8-Bromo-2'-Deoxyguanosine
8-Bromoguanine
8-Bromoguanosine
8-Bromoinosine
6-Bromopurine
6-Carboxymethymercaptopurine
2-Chloroadenosine
5'-Chloro-5'-Deoxyadenosine
5'-Chloro-5'-Deoxyinosine
8-Chloro-2,6-Dihydroxypurine
6-Chloroguanine
6-Chloroguanine Riboside
6-Chloroguanosine
6-Chloropurine
6-Chloropurine Riboside
8-Chloroxanthine
CORDYCEPIN ™
6-Cyanopurine
2,6-Dichloropurine
2'-3'-Dideoxyadenosine
2'-3'-Dideoxyguanosine
2,8-Dihydroxyadenine
2,6-Dihydroxy-1-Nethylpurine
2,6-Dihydroxypurine
2,6-Dihydroxypurine

TABLE II-continued

PURINE ANALOGS

6-Dimethylaminopurine
6-Dimethylaminopurine-9-Riboside
1,1-Dimethylguanidine
1,7-Dimethylguanine
1,7-Dimethylguanosine
N'-Dimethylguanosine
1,7-Dimethylxanthine
3,7-Dimethylxanthine
2,8-Dithio-6-Oxypurine
2,6-Dithiopurine
1,N'-Ethenoadenosine
6-Ethoxypurine
9-Ethyladenine
5'-(N-ethyl)-Carboxamidoadenosine
9-Ethylguanine
6-Ethylmercaptopurine
6-n-Heptylmercaptopurine
6-n-Hexylaminopurine
6-Histaminopurine
N'-(2-Hydroxyethyl)Adenosine
6-(β-Hydroxyethylamino)Purine
1-Hydroxy-iso-Guanine
2-Hydroxy-6-Mercaptopurine
6-Hydroxy-2-Mercaptopurine
2-Hydroxy-6-Methylpurine
6-Hydroxy-1-Methylpurine
2-Hydroxypurine
6-Hydroxypurine
2-Hydroxy-6-Thiopurine
6-Hydroxy-2-Thiopurine
5'-Iodo-5'-Deoxyadenosine
6-Iodopurine
N'-(Δ'-Isopentenyl)Adenosine
6-Isopropoxypurine
2',3'-O-Isopropylideneadenosine
2',3'-O-Isopropylideneguanosine
2',3'-O-Isopropylideneinosine
2',3'-O-Isopropylidene-6-Thioinosine
2-Mercaptoinosine
2-Mercaptopurine
6-Mercaptopurine
6-Mercaptopurine Arabinoside
6-Mercaptopurine 2'-Deoxyriboside
6-Mercaptopurine Riboside
2-Mercaptopyrimidine
6-Methoxypurine
6-Methoxypurine Riboside
1-Methyladenine
2-Methyladenine
3-Methyladenine
1-Methyladenosine
2'-O-Methyladenosine
3'-O-Methyladenosine
6-Methylaminopurine
1-Methylguanine
7-Methylguanine
1-Methylguanosine
2'-O-Methylguanosine
3'-O-Methylguanosine
7-Methylguanosine
1-Methylhypoxanthine
1-Methylinosine
7-Methylinosine
Methylmercaptoguanine
6-Methylmercaptopurine
6-Methylmercaptopurine Riboside
6-Methylpurine
6-n-Propoxypurine
6-n-Propylmercaptopurine
6-Selenoguanosine
6-Selenoinosine
6-Selenopurine
6-Thioguanine
6-Thioguanosine
8-Thioguanosine
Thiohydroxypurine
2-Thioxanthine

TABLE II-continued

PURINE ANALOGS

6-Thioxanthine
2,6,8-Trichloro-7-Methylpurine
2,6,8-Trichloropurine
1,3,9-Trimethylxanthine
2,6,8-Trioxypurine Examples of prodrugs which may be metabolizable by hepatic aldehyde oxidase to a corresponding uridine, thymidine, cytidine, guanosine, 8-azaguanine or 6-azauradine analog are the following:

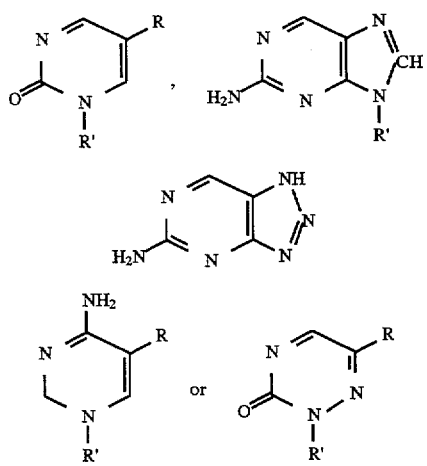

wherein

R is I, F, Br, Cl, H, —$CH_3$, —$OR^1$, —$CF_3$, $NO_2$, $SR^1$, —$CH=CR^2R^3$, —$C\equiv CR^2$ or —$N=N^+$—$N^-$, $R^1$ is an alkyl group from 1 to 5 carbon atoms, preferably having one carbon atom, $R^2$ and $R^3$, independently of each other, are hydrogen, a $C_1$-$C_5$-alkyl group or a halogen, and R' is hydrogen, a sugar residue such as ribose or deoxyribose, —$CH_2$—O—$CH_2$—$CH_2OH$, —$CH_2$—O—$CH(CH_2OH)$, substituted or unsubstituted alkyl, aryl, cycloalkyl, cycloaryl or any other desired residue which is not of such size as to sterically hinder the action of the hepatic aldehyde oxidase. It has been shown that this residue does not interfere with the desired action of the hepatic aldehyde oxidase on the compound.

Preferred groups for —$CH=CR^2R^3$ are —$CH=CF_2$ and —$CH=CH_2$. R sugar analogs are preferably

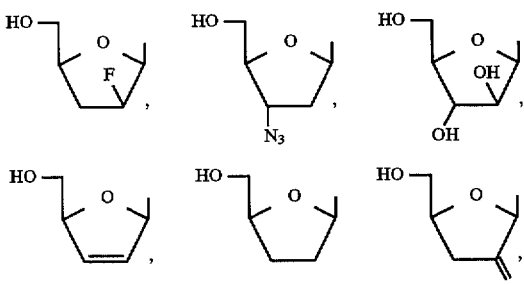

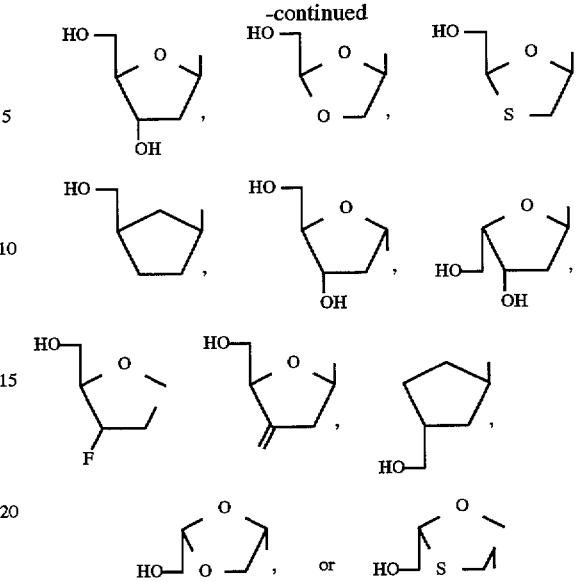

Esters of the sugar analogs for use in the invention include esters in which H of $HOCH_2$ in the analog is replaced by

in which the non carbonyl moiety $R^4$ of the ester grouping is selected from hydrogen, straight or branched chain alkyl (e.g., methyl, ethyl, n-propyl, t-butyl, n-butyl), alkoxyalkyl (e.g., methoxymethyl), aralkyl (e.g., benzyl), aryloxyalkyl (e.g., phenoxymethyl), aryl (e.g., phenyl optionally substituted by halogen, $C_{1-4}$ alkyl or $C_{1-4}$ alkoxy); substituted dihydropyridinyl (e.g., N-methyldihydro pyridinyl); sulphonate esters such as alkyl or aralkylsulphonyl (e.g., methanesulphonyl); sulphase esters; amino acid esters (e.g., L-valyl or L-isoleucyl) and mono-, di- or tri-phosphate esters.

Also included within the scope of such esters for use in the invention are esters derived from poly-functional acids containing more than one carboxyl group, for example, dicarboxylic acids $HO_2C(CH_2)_nCO_2H$ where n is an integer of 1 to 10 (for example, succinic acid) or phosphoric acids. Methods for preparing such esters are well known in the art.

With regard to the above described esters, unless otherwise specified, any alkyl moiety present advantageously contains 1 to 16 carbon atoms, preferably 1 to 4 carbon atoms and could contain one or more double bonds. Any aryl moiety present in such esters advantageously comprises a phenyl group.

In particular, the ester may be a $C_{1-6}$ alkyl ester, an unsubstituted benzoyl ester or a benzoyl ester substituted by at least one halogen (bromine, chlorine, fluorine or iodine), saturated or unsaturated $C_{1-6}$ alkyl, saturated or unsaturated $C_{1-6}$ alkoxy, nitro or trifluoromethyl groups.

Pharmaceutically acceptable salts of the above described analogs include those derived from pharmaceutically acceptable inorganic acids and bases. Examples of suitable acids include hydrochloric, hydrobromic, sulfuric, nitric, perchloric, fumaric, maleic, phosphoric, glycollic, lactic, salicylic, succinic, toluene-p-sulfonic, tartaric, acetic, citric, methanesulfonic, formic, benzoic, malonic, naphthalene-2-sulfonic and benzenesulfonic acids.

As used herein, the term "analog" (or "active ingredient") includes the analog itself, as well as an ester or salt thereof.

Salts derived from appropriate bases include alkali metal (e.g., sodium), alkaline earth metal (e.g., magnesium), ammonium and $NR_4^+$ (where R is $C_{1-4}$ alkyl) salts.

The choice of bio-affecting compounds for which prodrugs can be formed in accordance with the present invention is not limited solely to nucleoside or nucleoside base analogs. Virtually any compound having a keto group in its structure is a candidate for a prodrug metabolizable by hepatic aldehyde oxidase to that compound. Such can be determined by the simple assay discussed above.

The term "bio-affecting compound" or "biologically active substance" is intended to include compounds regulating any aspect of the metabolism of the animal to which it is to be administered or that of an organism invading the animal to which it is to be administered. These include, without limitation, anti-depressants, antibiotics, blood-pressure regulating drugs, analgesics; anti-neoplastics, antivirals, etc.

Therapeutic treatment of liver-associated diseases is a particularly preferred use of the prodrugs of the present invention due to the fact that the hepatic aldehyde oxidase was found substantially exclusively in the liver. Thus, a particular advantage of the prodrugs of the present invention is in the elimination and reduction of side-effects which would otherwise be caused by the systemic administration of the bio-affecting compound when it is desired to have its effect only in the liver. Many compounds, such as IUdR, which are useful when treating proliferating cells, have substantial systemic toxicity which have limited their clinical utility. The corresponding prodrug generally will not have the same activity as the bio-affecting compound. Thus, such prodrugs are generally non-toxic except when metabolized into the desired bio-affecting compound. For example, the 5-substituted pyrimidinone precursors for IUdR or FU are not substrates for human thymidine kinase and thymidine phosphorylase and are substantially non-toxic. When used for the treatment of hepatic carcinoma, for example, IPdR will be metabolized in the liver by the hepatic aldehyde oxidase to IUdR which will then be preferentially taken up by the tumor cells in the liver before substantial spread of the IUdR to other tissues can occur. Thus, the therapeutic index of the 5-substituted PdR compounds for primary liver cancer or metastatic liver cancer will be much better than their UdR counterparts.

There are other occasions besides the treatment of liver-associated diseases when the administration of a prodrug will be preferred to the administration of the bio-affecting compound which is formed from such prodrugs. For example, many drugs are not orally administrable for any of a variety of reasons. Oral administration of a prodrug from which the active compound is released in the liver will avoid most of the disadvantages of oral administration of the active compound. Thus, for example, FU is a well-known anti-cancer drug which cannot be administered orally. FP is a prodrug which is metabolizabie by hepatic aldehyde oxidase to FU. FP may be given orally to a subject. As is shown in the examples below, FP has demonstrated therapeutic effectiveness in leukemia and colon cancer. The effectiveness of FP is essentially the same as FU, indicating effective delivery of FU from the hepatocytes to the tumor.

Currently, IUdR and BUdR are being explored as radiosensitizers. However, their effective use is limited by their cytotoxicity and rapid catabolism to the free base, followed by dehalogenation (Speth, P. A. J., Kinsella, T. J., Chang, A. E., Klecker, R. W., Belanger, K. and Collins, J. M., (1988), Clin. Pharmacol. Ther. 44, 369–375). Since IPdR and its analogs are virtually non-toxic, and are not substrates for thymidine phosphorylase, the use of IPdR and its analogs instead of IUdR or BUdR will circumvent the difficulties of toxicity and degradation related to radiation therapy.

"Liver-associated diseases" include viral hepatitis, for example, hepatitis A, hepatitis B, hepatitis C and hepatitis D; hepatoma; cancers metastasized to and from the liver; infection with cytomegalovirus or other viruses, parasitic infections, e.g. Schistosomiasis, Clonorchiasis, Fascioliasis, Opisthorchiasis; and infection by an assortment of flukes and tapeworms, microbial agents, e.g. fungal or bacterial infections, such as *Paracoccidioides brasiliensis*, and other liver diseases, such as cirrhosis of the liver, or rejection of liver transplants.

Metabolic conditions or diseases are also treatable by selective use of a prodrug which is metabolizable into an active compound by the hepatic aldehyde oxidase. Drugs may be those which are targeted to receptors in or on liver cells as well as non-liver cells are also of value. These drugs may have either whole or partial agonist or antagonist activity. A great variety of receptor acting drugs may be created by administering the corresponding prodrug to a subject or to a preparation of the aldehyde oxidase in vitro. Thus prodrugs of drugs acting at remote sites such as the heart or brain, may also be used in accordance with the present invention. Furthermore, if liver cells lack the target receptors, the potential for unwanted toxicity due to high liver concentrations are reduced. The use of prodrugs metabolizable by a liver enzyme to active drugs has wide applicability.

Depending on the level of enzyme activity of the aldehyde oxidase on a prodrug, a slow rate of formation or slow release of active drug into the body may be achieved. While the compounds exemplified herein are rapidly metabolized, they can be modified to slow their metabolism. This should result in a requirement for less frequent dosages of prodrug compared to the drug, with all of the known advantages of patient compliance and constancy of dosage. If the metabolism to the active drug is sufficiently slow, entirely new classes of compounds may be used therapeutically which could not be used before due to toxicity problems with bolus dosages. It can be seen, for example, from Table V hereinbelow that the nature of the R group on the pyrimidinone substrate substantially effects the rate of conversion. Thus, it is clear that prodrugs can be designed with a predetermined rate of metabolism.

One example of a drug which would be improved by slow conversion in vivo is the ketone containing drug suramin. The effective anti-cancer dosage for metastatic prostate cancer is very close to the dosage resulting in paralysis, as was accidently and unfortunately discovered during human trials. Bolus dosages were found to be significantly less effective. As a consequence, patients requiring such treatment are hospitalized and continuously monitored and infused to maintain a narrow range of effective and acceptable concentrations. By using an aldehyde or other prodrug form of suramin metabolizable by aldehyde oxidase to active suramin, it should be possible to give the patient bolus doses without a need for constant hospitalization.

As indicated above, orally acceptable prodrugs may be used in place of their active product which are not orally acceptable. A prodrug may differ from its active product by increased stability in acidic conditions, resistance to digestive enzymes, better adsorption or less irritation or toxicity to the digestive system. Once adsorbed, the prodrug is converted to the active drug by liver aldehyde oxidase, thereby bypassing the digestive track. The advantages of oral versus parenteral administration are readily apparent to those skilled in the art.

Regardless of the route of administration, any drug has half-life limitations due to renal clearance, enzymatic degradation, and too much or too little binding to serum proteins and the like. The use of prodrugs broadens the opportunities for drug development by compensating for such problems.

The amount of the analog described above for use in the present invention will vary not only with the particular compound selected, but also with the route of administration, the nature of the condition being treated and the age and condition of the patient and will be ultimately determined by the discretion of the attendant physician or veterinarian. In general, however, a suitable dose will be in the range from about 1 to about 100 mg/kg of body weight per day, preferably about 2 to about 50 mg per kilogram body weight per day, most preferably 2 to 10 mg/kg/day.

The desired dose may conveniently be presented in a single dose or as divided doses administered at appropriate intervals, for example, at two, three, four or more sub-doses per day.

The analog as described above is conveniently administered in unit dosage; for example, containing 0.5 to 50 mg, preferably 20 to 1000 mg, most preferably 50 to 700 mg, of active ingredient per unit dosage form.

Ideally, the active ingredient should be administered to achieve peak plasma concentrations of the active ingredient of from about 1 to 75 µM, preferably about 2 to 50 µM, most preferably about 3 to about 30 µM. This may be achieved, for example, by the intravenous injection of 0.1 to 5% solution of the prodrug, optionally in saline, or administered as a bolus containing about 0.1 to 50 mg/kg of the active ingredient.

It will be appreciated that different prodrugs may require vastly different dosages. Furthermore, treatment of diseases of different tissues or organs may also require different dosages. These dosages are readily determinable by one of ordinary skill in the art using methods known in the art.

While it is possible that, for use in therapy, the analog described above may be administered as the raw chemical, it is preferable to present the prodrug in conjunction with a pharmaceutically acceptable carrier as a pharmaceutical formulation.

The invention thus further provides a pharmaceutical formulation comprising an analog as described together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient therefor.

Pharmaceutical formulations include those suitable for oral, rectal, nasal, topical (including buccal, sub-lingual and transdermal), vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active ingredient with liquid carriers or finely divided solid carriers or both and then, if necessary, shaping the product into the desired formulation. Encapsulation of the chemical, such as by a liposome or vesicle, may also be used where indicated for delivery or stabilization purposes.

Pharmaceutical formulations suitable for oral administration may conveniently be presented as discrete units such as capsules, cachets or tablets each containing a predetermined amount of the active ingredient; as a powder or granules; as a solution; as a suspension; or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspension, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils) or preservatives.

The active ingredient may also be formulated for parental administration (e.g., by injection, for example, bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulary agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

Pharmaceutical formulations suitable for rectal administration, wherein the carrier is a solid, are most preferably represented as unit dose suppositories. Suitable carriers include cocoa butter and other materials commonly used in the art, and the suppositories may be conveniently formed by admixture of the active compound with the softened or melted carrier(s) followed by chilling and shaping in molds.

Formulations suitable for vaginal administration may be presented as pessaries, tampons, creams, gels, pastes, foams or sprays containing in addition to the active ingredient, such carriers as are known in the art to be appropriate.

For intra-nasal administration, the active ingredient may be used as a liquid spray or dispersible powder or in the form of drops.

Drops may be formulated with an aqueous or non-aqueous base comprising one or more dispersing agents, solubilizing agents or suspending agents. Liquid sprays are conveniently delivered from pressurized packs.

For administration by inhalation, the active ingredient is conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the active ingredient may take the form of a dry powder composition, for example, a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

When desired, the above described formulations adapted to give sustained release of the active ingredient may be employed.

The pharmaceutical compositions for use according to the invention may also contain other active ingredients such as antimicrobial agents or preservatives.

The pharmaceutical composition for use according to the present invention may also contain inert ingredients such as desiccants, substances to provide ease of handling, colorants, flavorants and coatings for easy swallowing.

The active ingredient may also be used in combination with other therapeutic agents, for example, other anti-infective agents. In particular, the compounds of formula (I) may be employed together with well known antiviral agents, e.g., adenine arabinoside or interferon α.

The invention thus provides, in a further aspect, a method comprising the use of an analog described above with another therapeutically active agent, in particular, an anti-HBV agent.

When the active ingredient generated from the prodrug is an anti-cancer agent, other anti-cancer or immunomodulating agents may be employed together, as may any other compatible combination of drugs whether the activities are synergistic, complementary of separate.

The combinations referred to above may conveniently be presented for use in the form of a pharmaceutical formulation and thus the use of pharmaceutical formulations comprising a combination as defined above together with a pharmaceutically acceptable carrier therefor comprise a further aspect of the invention.

The individual components of such combinations may be administered either sequentially or simultaneously in separate or combined pharmaceutical formulations.

When an analog as described above is used in combination with a second therapeutic agent for the same disease, e.g. active against the same virus, the dose of each compound may be either the same or different from that when the analog is used alone. The appropriate dose will be readily appreciated by those skilled in the art.

The aldehyde oxidase is advantageously purified from liver and may be immobilized on a solid phase for easy separation of enzyme catalyst from a reaction mixture. The desired bio-affecting optically active compounds are then separated from procompound precursors and recovered. Techniques for enzyme purification are well known in the art, any suitable one of which may be employed. Techniques for enzyme immobilization to a solid phase whether it be adsorbed, entrapped, chemically bound or retained behind a semipermeable membrane are also well known in the art.

The contents of all references mentioned in this application are incorporated by reference. The invention will now be described with reference to the following non-limiting examples.

EXAMPLES

Example 1

Tissue Preparation

Rat hepatic tissue was washed with ice-cold 1.15% KCl and blotted dry. The tissue was then homogenized with a tissue homogenizer, in a volume of 1.15% KCl that was 3 times the tissue weight, to form a 25% (w/v) homogenate. The homogenate was then centrifuged at 10,000 g for 10 minutes at 4° C. The resulting supernatant was filtered through Miracloth (similar to cheese cloth) then dialyzed overnight against 50 mM Tris-HCl buffer pH 7.5 and stored at −80° C. before use. Rat hepatocytes were obtained by a perfusion technique then the cells were extracted with 10 mM phosphate buffer, pH 7.5, containing 1M KCl and dialyzed for 4 hours against 50 mM Tris-HCl buffer pH 7.5.

Example 2

Assay Conditions

For the standard assay condition, the reaction mixture contained 50 mM Tris-HCl, pH 7.5, 1 mM EDTA, 180 µM of IPdR (or its analogs) and approximately 0.01 mg protein of 10,000 g supernatant of tissue homogenate in a final volume of 500 µl and the incubation was at 37° C. for 10 minutes unless specified otherwise. 300 µl of reaction mixture was removed at the end of incubation and mixed with 630 µl acetonitrile then agitated. The precipitated protein were removed by centrifugation and the supernatant was lyophilized to dryness. The samples were reconstituted to the original aliquot volume with the HPLC mobile phase buffer and analyzed on a Alltech RP-18 column. IPdR, IUdR and IU were detected at a UV absorption wavelength of 230 nm, and IPdR was also detected at a UV absorption wavelength of 335 nm. The mobile phase was 10% acetonitrile/ 90% mM ammonium acetate, pH 6.8 and the flow rate was 1 ml/minute. Standard curves of IPdR and IUdR were established from the integration value of known concentrations.

Example 3

Conversion of 5-iodo-2-pyrimidinone-2'-deoxyribose (IPdR) to 5-iodo-deoxyuridine (IUdR)

To study the conversion of IPdR to IUdR by liver enzyme the metabolites of IPdR were analyzed after incubation with a supernatant of rat liver homogenate using a reverse phase HPLC technique. IPdR and IUdR could be detected at an absorption wavelength of 230 nm but only IPdR could be detected at 335 nm. In order to limit the phosphorolytic cleavage of IUdR to iodouracil (IU) by thymidine phosphorylase (Kinsella, T. J., Mitchell, J. B., Russo, A., Morstyn, G. and Glatstein, E., (1984), *J. Radiation Oncology Biol. Phys.*, 10, 1399–1406), Tris-HCl buffer was employed in the assay. As shown in FIG. 1, there was a time dependent conversion of IPdR to IUdR and IUdR appeared to be the only product produced by IPdR. The identification of IUdR was confirmed based on the retention time on a C-18 column (8 minutes vs. 9.5 minutes for IPdR) and the UV spectrum as well as nuclear magnetic resonance spectroscopy (results are not shown).

Example 4

Properties of "IPR oxidase" activity

This "IPdR oxidase" activity does not require exogenous cofactors, is much less active in extracts of kidney and spleen than liver (Table III) and cannot be detected in lung or intestine extracts from rats. The human liver contains a similar amount of this enzyme. Extracts of hepatocytes, which represents about 80% of the cell population in liver, had a very similar specific activity compared with the whole liver extract, suggesting that the IPdR oxidation is mainly present in this cell population. Differential fractionation centrifugation was used in an attempt to localize this IPdR conversion enzyme activity in the liver homogenate. The enzyme activity assay was performed on each fraction. The only fraction which showed the enzyme activity appeared in the 100,000 g×60 minutes supernatant; this suggested that this enzyme is only located in the soluble fraction of cytosol. Further purification was achieved by use of DEAE cellulose column chromatography, blue Sepharose column chromatography and glycerol gradient centrifugation in this order. This IPdR oxidase activity was purified 380 fold starting from the crude extracts of rat liver. The partially purified enzyme catalyzed IUdR synthesis at a rate of 3.8 µmoles per minute per milligram of protein at 37° C. under these conditions. The apparent molecular weight of this enzyme in both rats and humans as determined by centrifugation on a 20 to 40% glycerol gradient is approximately 280,000 dalton. Neither cofactor nor divalent cations requirement has been found for the rat liver enzyme or the human liver enzyme.

TABLE III

Tissue specificity of the conversion of IPdR to IUdR by cell extracts

| Tissue (or cells) | Specific activity[a] (n mole/mg protein/min) |
|---|---|
| liver (human) | 2–7 |
| liver (rat) | 5–15 |
| hepatocyte (rat) | 5–11 |
| kidney (rat) | 0.8–1.6 |
| spleen (rat) | 0.2–0.5 |
| intestine (rat) | <0.02[b] |
| lung (rat) | <0.02[b] |

[a]The specific activities were obtained from 3 samples for each tissue (also 3 samples for rat hepatocyte) except the data for rat liver which were obtained from 5 samples.
[b]The conversion of IPdR to IUdR by rat, lung and intestine was not detected.

Example 5 identification of "IPdR oxidase"

In order to determine which enzyme is responsible for the catalysts of this IPdR oxidation, a series of known oxidoreductases which have similar capability to oxidize a carbon atom with an adjacent amino group into a carbonyl functionality were explored for their ability to catalyze IPdR oxidation. Xanthine oxidase (Boehringer Mannheim) isolated from cow milk which catalyzes the oxidation of hypoxanthine to xanthine failed to convert IPdR to IUdR. A mixed function oxidase system prepared from the microsome of rat liver a broad spectrum of substrates and is NADPH dependent. However, this microsoma fraction from rat liver showed no IPdR oxidase activity no matter whether NADPH was added or not. Alcohol dehydrogenase (which can be obtained from Sigma) and alcohol oxidase (which can be obtained from Sigma) both reside in the soluble fraction of liver cell extracts, but the conversion of IPdR to UdR was not detected with purified preparation of either enzyme under the same conditions that they converted their natural substrates effectively. Sarcosine oxidase (Boehringer Mannheim) which catalyzes the conversion of $N^1$-methylglycine to glycine had no IPdR oxidase activity. Phenylalanine hydroxylase, urocanase, cystathionine γ-lyase, L-glutamate dehydrogenase, cystathionase and several other oxido-reductases were ruled out based on substrate competition assays, their different cofactor specificities or some other characteristic features from literature (Weidig, C. F., Halvorson, H. R. and Shore, J. D., (1977), Biochemistry 16, 2916–2921; Kato, N., Omori, Y., Tani, Y. and Ogata, K., (1976), Eur. J. Biochem., 64, 341–350; Keul, V., Kaeppeli, F., Ghosh, C., Krebs, T., Robinson, J. A. and Retey, J., (1979), J. Biol. Chem., 254, 843–851; George, D. J. and Phillips, A. T., (1970), J. Biol. Chem., 245, 528–537; Brodie, B. B., Axelrod, J., Cooper, J. R., Gaudette, L., LaDu, B. N., Mitoma, C. and Udenfriend, S., (1955), Science, 121, 603–604; Eeme, D., Durieu-Trautmann, O. and Chatagner, F., (1971), Eur. J. Biochem., 20, 269–275).

Since hepatic aldehyde oxidase has the same molecular weight, is in the cytosolic fraction of liver cells and has broad substrate specificity (Rajagopalan, K. V., Fridovich, I. and Handler, P., (1962), J. Biol. Chem., 237, 922–928), it is considered that it is the "IPdR oxidase" enzyme responsible for the conversion of IPdR to IUdR. Hepatic aldehyde oxidase which catalyzes the oxidation of a variety of aldehydes to the corresponding acids also converts $N^1$-methylnicotinamide (Sigma) to $N^1$-methyl-2-pyridone-5-carboxamide and $N^1$-methyl-4-pyridone-3-carboxamide (Rajagopalan, K. V., Fridovich, I. and Handler, P. (1962), J. Biol. Chem., 237, 922–928; Rajagopalan, K. V. and Handler, P., (1964), J. Biol. Chem. 239, 2022–2035; Stanulovic, M. and Chaykin, S., (1971), Archs. of Biochem. and Biophy., 145, 27–34; Stanulovic, M. and Chaykin, S., (1971), Archs. of Biochem. and Biophy., 145, 35–42; Felsted, R. L., Chu, A. E. and Chaykin, S., (1973), J. Biol. Chem., 248, 2580–2587; Barber, M. J., Coughlan, M. P., Rajogopalan, K. V. and Siegel, L. M., (1982), Biochemistry, 21, 3561–3568; Badwey, J. A., Robinson, J. M., Karnovsky, M. J. and Karnovsky, M. L., (1981), J. Biol. Chem., 256, 3479–3486). This aldehyde oxidase activity was reported to be stimulated by potassium ferricyanide and Tris buffer but not by $MgCl_2$ (Felsted, R. L., Chu, A. E. and Chaykin, S., (1973), J. Biol. Chem., 248, 2580–2587. This enzyme could be inhibited by 2-mercaptoethanol, dithiothreitol and other thiol agents (Rajagopalan, K. V. and Handler, P., (1964), J. Biol. Chem. 239, 2022–2035). There was no significant inhibition by cysteine at 5 mM, however at 50 mM a potent inhibition of the enzyme activity was observed (Felsted, R. L., Chu, A. E. and Chaykin, S., (1973), J. Biol. Chem., 248, 2580–2587). Divalent metal cations such as $Cu^{++}$, $Zn^{++}$ and $Fe^{++}$ caused strong inhibition (Rajagopalan, K. V., Fridovich, I. and Handler, P., (1962), J. Biol. Chem., 237, 922–928). The activity could also be inhibited by acetaldehyde, but not by allopurinol or formaldehyde (Rajagopalan, K. V. and Handler, P., (1964), J. Biol. Chem., 239, 2022–2035; Stanulovic, M. and Chaykin, S., (1971), Archs. of Biochem. and Biophy., 145, 35–42; Badwey, J. A., Robinson, J. M., Karnovsky, M. J. and Karnovsky, M. L., (1981), J. Biol. Chem., 256, 3479–3486). Therefore a series of compounds were examined for their effects on the oxidation of IPdR to IUdR and it was found that the inhibition profile of compounds with the "IPdR oxidase" activity (Table IV) was essentially identical to the characteristic pattern of aldehyde oxidase. Furthermore, throughout each step of the purification, aldehyde oxidase could not be separated from "IPdR oxidase" activity.

TABLE IV

Effect of inhibitors on the oxidation of IPdR to IUdR by liver homogenate

| Compound tested | $IC_{50}$ (mM)[a] |
|---|---|
| Mercaptoethanol | 1.8 |
| Dithiothreitol | 0.1 |
| Cysteine[b] | >50 |
| 1-Butane thiol[c] | >50 |
| SKF-525A (Calbiochem) | 0.03 |
| Hydroxyl amine | 1 |
| Hydrogen peroxide | 10 |
| $Cu^{++}$ | 0.4 |
| $Zn^{++}$ | 0.3 |
| $Fe^{++}$ | 4 |
| Acetaldehyde | 5 |
| $N^1$-methylnicotinamide | 1 |

[a]The concentrations of each compound at 50% inhibition of the conversion of IPdR to IUdR.
[b]Approximately 40% product inhibition was observed at 50 mM.
[c]Approximately 25% product inhibition was observed at 50 mM.

Example 6

Substrate Specificity

Several 2-pyrimidinone deoxyribose analogs were examined for the conversion to their deoxyuridine counterparts.

The Michaelis constant Km for IPdR in the reaction at pH 7.5 and pH 9.5 is 150 μM and 87 μM respectively, and the Km for 5-ethynyl-2-pyrimidinone deoxyribose (EPdR) in the reaction at pH 7.5 and pH 9.5 is 77 μM and 46 μM respectively. Nevertheless the relative Vmax for IPdR in the reaction at pH 7.5 and pH 9.5 is the same. 5-iodo-2-pyrimidinone (IP), the aglycose of IPdR was an excellent substrate for aldehyde oxidase. The synthetic substrates for aldehyde oxidase appear to be better than its natural substrates, $N^1$-methylnicotinamide and acetaldehyde, as judged by the potency of inhibition of $N^1$-methylnicotinamide and acetaldehyde to the IPdR oxidation reaction (Table IV). The rate of reactivity of the liver enzyme with different IPdR analogs follows the order EPdR, IP, IPdR, 5-bromo-2-pyrimidinone deoxyribose (BPdR) and 5-methyl-2-pyrimidinone deoxyribose (MPdR) or 5-ethyl-2-pyrimidinone deoxyribose (EtPdR) (Table V). Electronegative substituents in the 5-position seemed to increase the substrate activity in this oxidation reaction.

TABLE V

Substrate specificity of the conversion of RPdR to RUdR[a]

| R | R' | Substrate abbreviation | Rate of conversion[b] (n mole/mg/min) | Product Abbreviation |
|---|---|---|---|---|
| C≡CH | dR[c] | EPdR | 20 ± 4 | EUdR |
| I | dR | IPdR | 11 ± 2 | IUdR |
| I | H | IP | 18 ± 3 | IU |
| Br | dR | BPdR | 7 ± 2 | BUdR |
| $CH_3$ | dR | MPdR | <0.1[d] | MUdR |
| $CH_2CH_3$ | dR | EtPdR | <0.1[d] | EtUdR |
| F | H | FP | 20 | FU |

[a]Amount of substrate used was 180 μM in all cases.
[b]Determined based on 2 to 4 separate experiments.
[c]C = deoxyribose
[d]Products of the reaction from MPdR and EtPdR were not detected.

Example 7

Toxicity of FU and FP

Figure 2:
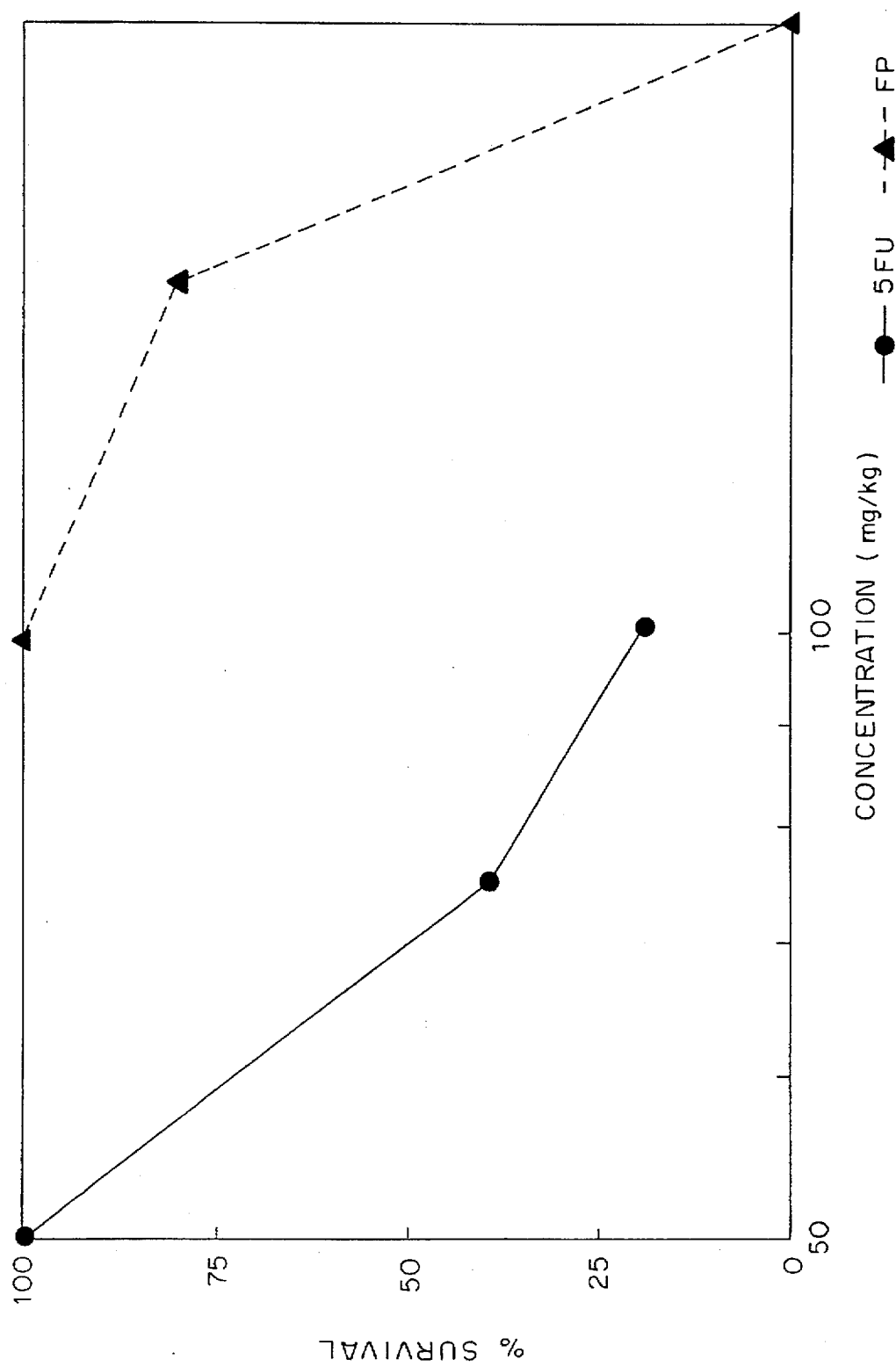
FIG. 2 depicts the survival rate of mice given 100 mg/kg daily oral dosages of FU and FP for five days.
Figure 3:
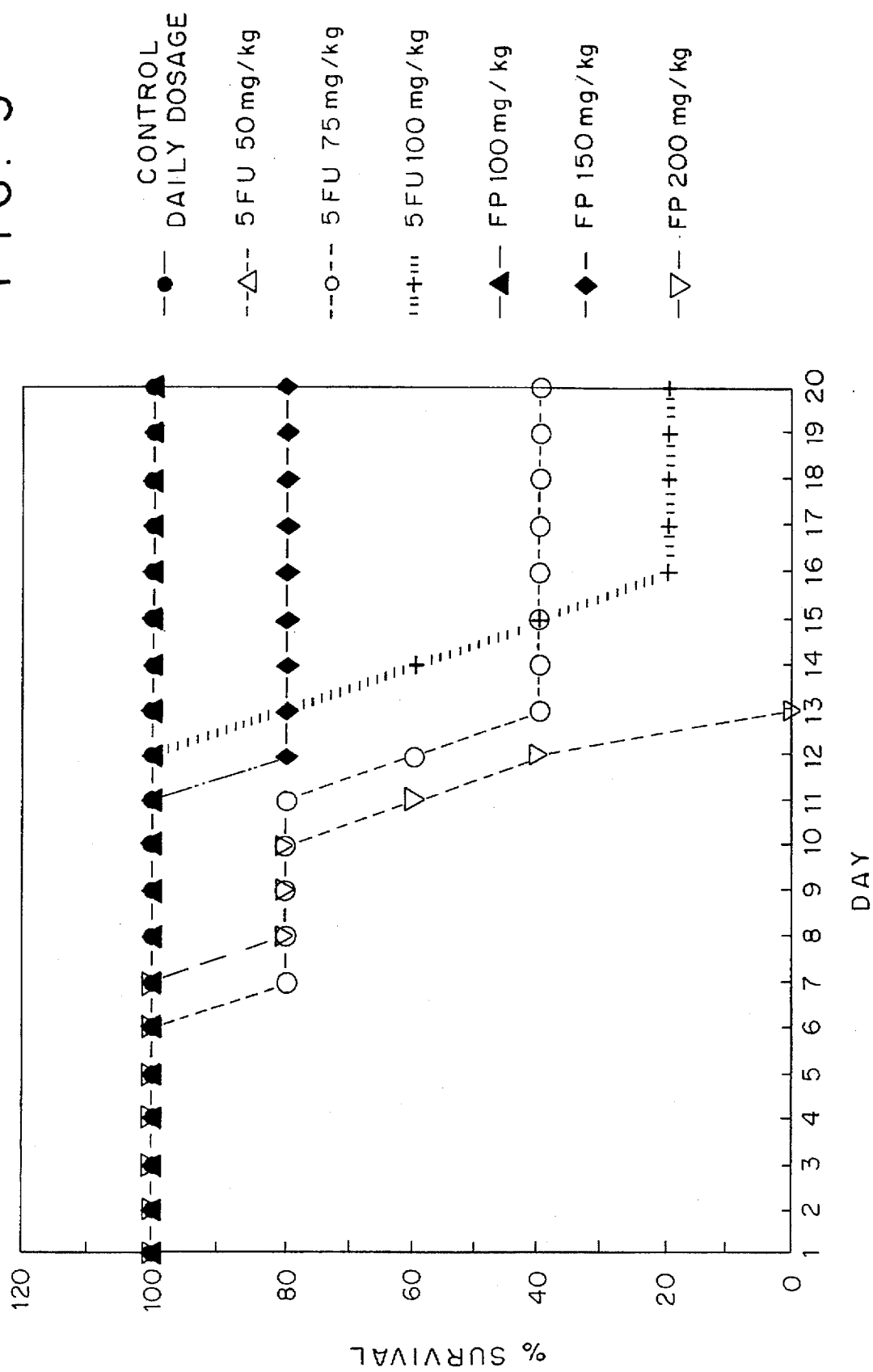
FIG. 3 depicts the survival rate of mice treated with varying dosages of FU and FP given orally.

BDF1 mice were administered daily oral dosages of either 50, 75 or 100 mg/kg of FU or 100, 150 or 200 mg/kg of FP. The survival rates of each are presented in chart and graphic forms in Table VI and FIGS. 2 and 3. The toxicity of FP was considerably less, even when higher dosages were administered.

TABLE VI

TOXICITY OF FU AND FP IN BDF1 MICE

| Compound | Schedule of Injection | Dose (mg/kg) | Route of injection | Death/ Total | $LD_{50}$ (mg/kg) Daily |
|---|---|---|---|---|---|
| FU | Day 1,2,3,4,5 | 50 | p.o. | 5/5 | 70 |
|  |  | 75 |  | 2/5 |  |
|  |  | 100 |  | 1/5 |  |
| FP |  | 100 | p.o. | 5/5 | 180 |

TABLE VI-continued

TOXICITY OF FU AND FP IN BDF1 MICE

| Compound | Schedule of Injection | Dose (mg/kg) | Route of injection | Death/ Total | $LD_{50}$ (mg/kg) Daily |
|---|---|---|---|---|---|
|  |  | 150 |  | 4/5 |  |
|  |  | 200 |  | 0/5 |  |

Example 8

Effects of FU and FP on Leukemia Cells

Figure 4:
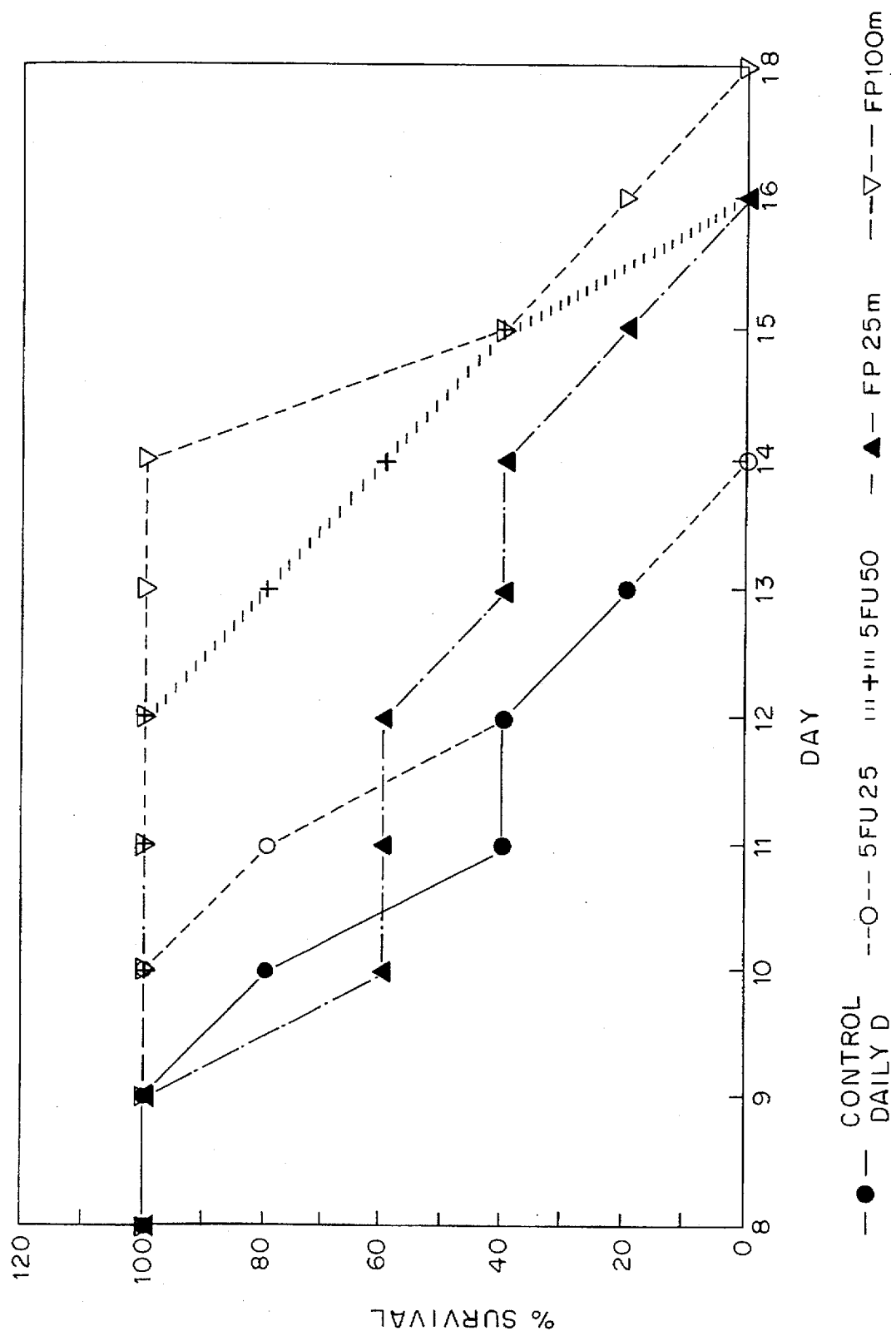
FIG. 4 depicts the survival rate of mice previously injected with leukemia cells and later administered varying concentrations of FU and FP given orally.

Mice were injected with 100,000 P388-R leukemia cells to induce a leukemia. These cells were resistant to Adriamycin. Daily treatments of 25 and 50 mg/kg FU and 50 and 100 mg/kg FP were given orally to these leukemic mice and the duration of survival was measured. The results are given in tabular and graphic form in Table VII and FIG. 4. The survival time was as long using FP compared to FU.

TABLE VII

EFFECT OF FU AND FP ON SURVIVAL TIME OF MICE BEARING LEUKEMIA CELLS

| Group | Number of Animals | Treatment[a] (Day) | Dose (mg/kg) | ILS[b] (%) | Cures/ Total |
|---|---|---|---|---|---|
| FU | 5 | Daily on Day 1,2,3,4,5 | 25 | 5 | 0/5 |
|  |  |  | 50 | 25 | 0/5 |
| FP | 5 |  | 50 | 0 | 0/5 |
|  |  |  | 100 | 30 | 0/5 |

Inoculum: $10^6$ P388-R cells into each mouse (i.p.)
[a]Treatment days are those days at which the animals received injections of the drug (day of tumor inoculation is Day 0)
[b]ILS, Increase in life span over controls which is expressed in terms of dying mice.

Example 9

Effects of FU and FP on Colon Carcinoma

Figure 5:
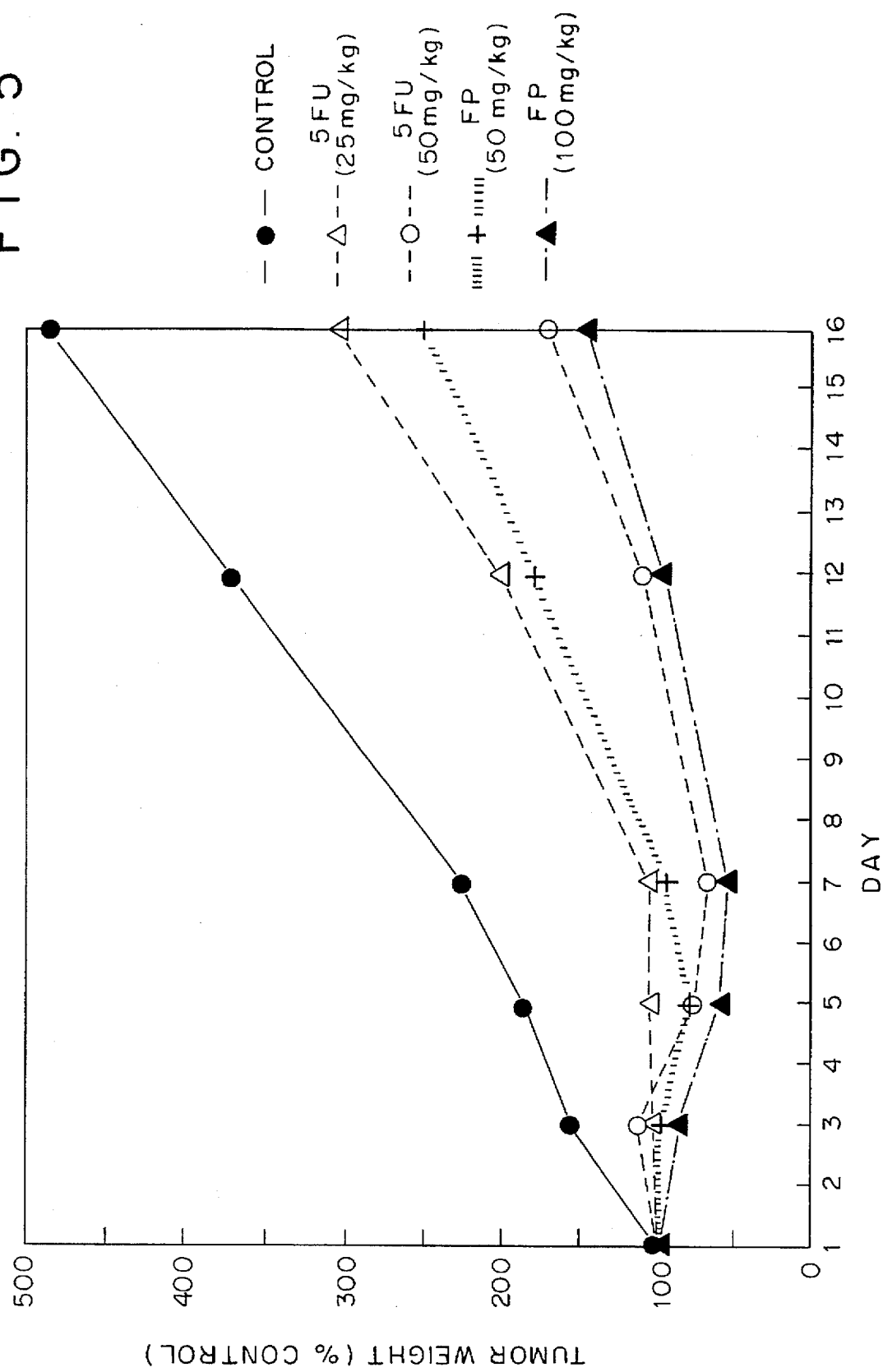
FIG. 5 depicts the change in weight of a colon tumor treated with various dosages of FU and FP given orally over time. All weight figures are given compared to an initial control.

Mice were injected with colon 38 cells and were either not treated or treated with daily treatments of 25 and 50 mg/kg FU and 50 and 100 mg/kg FP were given orally to the mice and the change in tumor weight was measured over time. The data is displayed in FIG. 5. The reduction in tumor size or reduction in its growth rate is comparable between FU and FP.

Example 10

Effects of IPdR Incorporation into Tissue of Athymic Nude Mice

Figure 6:
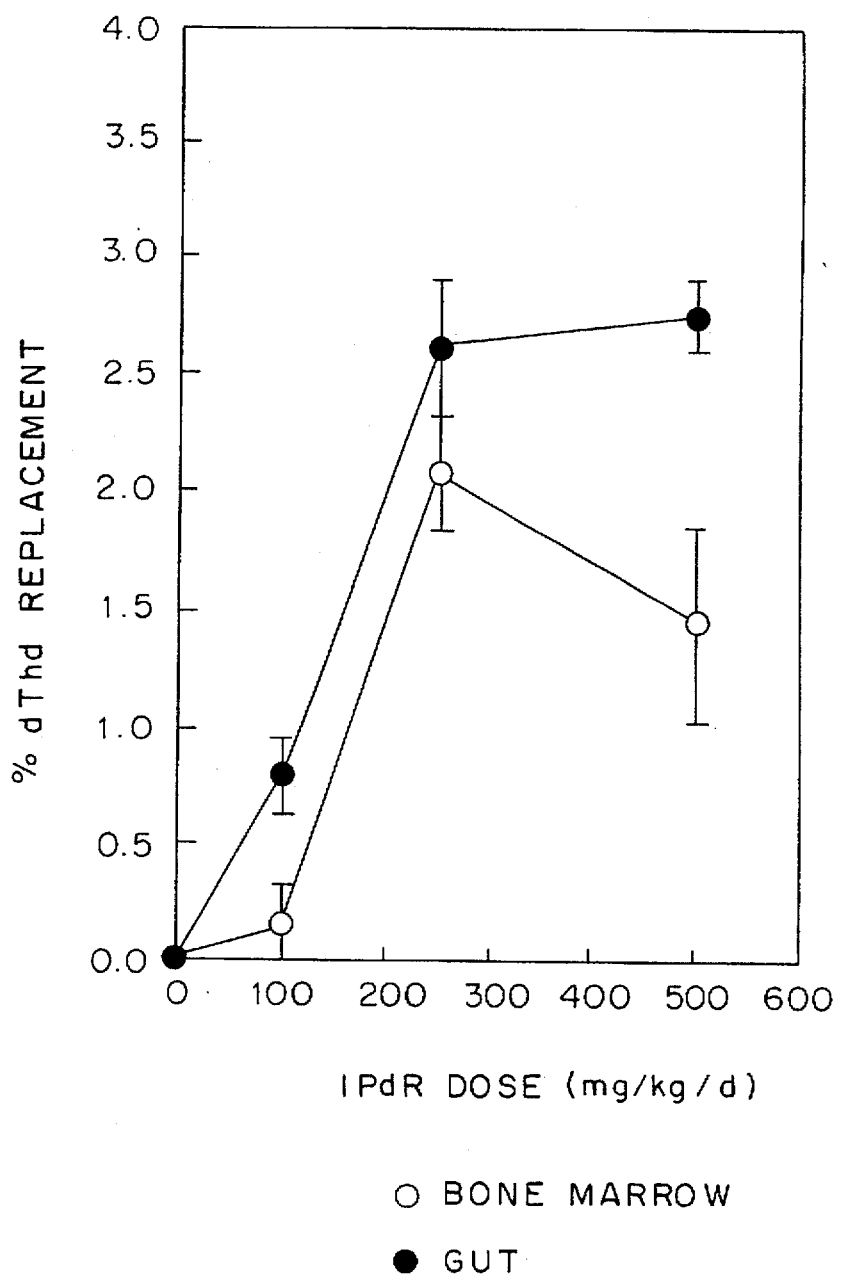
FIG. 6 depicts the relatively low IPdR incorporation into tissues of athymic nude mice in bone marrow and gut, wherein thymidine replacement plateaus at about 250 mg/kg/d.

Mice were administered daily oral dosages of 0, 100, 250 and 500 mg/kg. Percent dThd replacement as indicative of IPdR incorporation into bone marrow, gut and liver tissue was assayed according to known methods. As presented in FIG. 6, relatively small amounts of thymidine was replaced by IPdR in bone marrow and gut, with thymidine replacement plateaus occurring at treatment levels above 250 mg/kg/d. No incorporation of IUdR into liver was found. Results presented in FIG. 6 are mean percent thymidine replacement ± one standard error of the mean. N is greater or equal to 3 for each dose. As shown by these results, no appreciable thymidine replacement by IUdR occurred in liver, and very small percent replacement was found in bone marrow and gut. Accordingly, these results establish that the administration of IPdR used as a prodrug according to the present invention should be suitable for treatment of mammals including humans.

Example 11

IPdR Incorporation into Tissues of Athymic Nude Mice Having Metastatic Tumors

Figure 7:
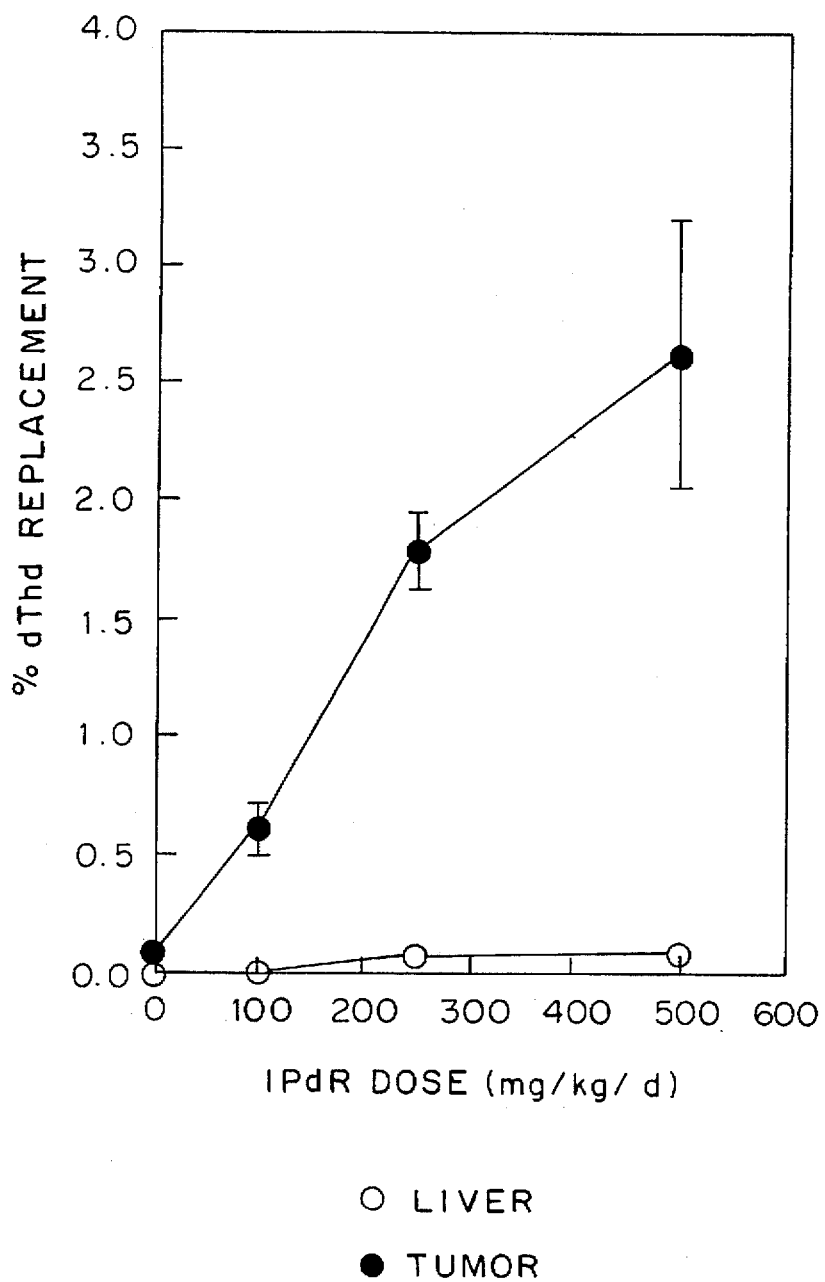
FIG. 7 depicts the comparative IPdR replacement into liver and tumor tissues of athymic nude mice between liver tissue and metabolic tumors, wherein liver incorporation was negligible compared to increasing tumor incorporation.

Mice were administered daily dosages of 0, 100, 250 and 500 mg/kg/d to determine thymidine replacement in liver and tumor tissue. The results presented in FIG. 7 are presented as mean percent thymidine replacement ± one standard error of the mean. $n \geq 3$ (control tumors n=2). While a very small percent incorporation was detected in normal liver, an increasing percent replacement was shown in the tumor, thus demonstrating that the use of IPdR as a prodrug for tumor treatment is expected to have good results.

Example 12

Treatment of Transgenic Mice by FP

Figure 8:
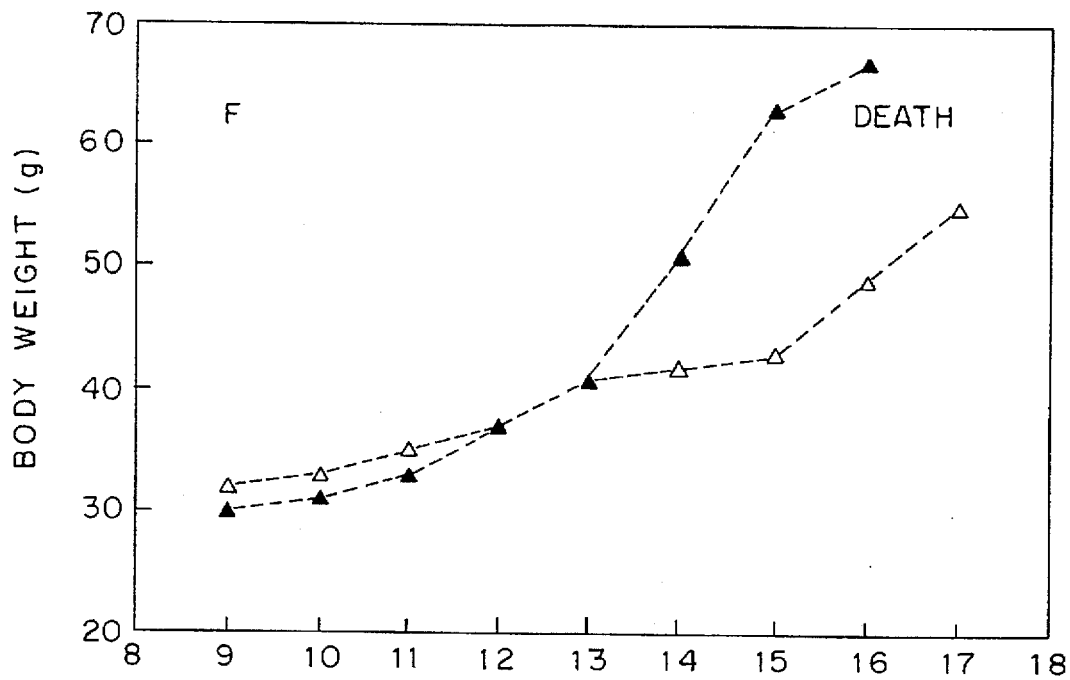
FIG. 8 depicts results of FP treatment of female transgenic mice expressing the SV40 large tumor antigen and developing various cancers, wherein FP treated mouse lived longer and had slower increase in body weight than a control.
Figure 9:
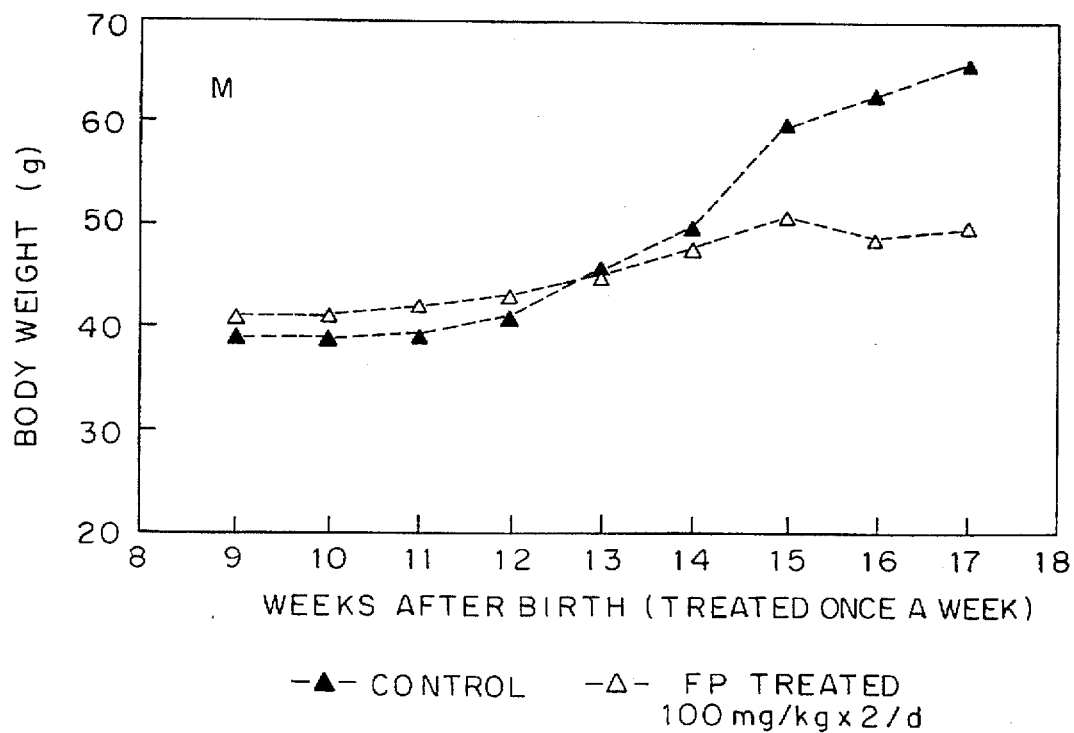
FIG. 9 depicts results of FP treatment of male transgenic mice expressing the SV40 large tumor antigen and developing various cancers, wherein FP treated mouse had a slower increase in body weight indicating longer survival than control.

Transgenic mice obtained according to the method of Sepulveda et al., Cancer Research 49:6108–6117 (1989) were administered beginning at nine weeks after birth in a female and male, wherein the treatment group received 100 mg/kg two times per day, once per week. FIGS. 8 and 9 show the change in body weight over weeks 9–17 for female and male mice, respectively. Both male and female treated mice showed a significantly decreased weight gain after week 13, which correlates to increased survival time. The female treated rat survived the control rat which died of cancer complications at week 16. Accordingly, the above data suggests that the use of FP as a tumor treatment according to the presently claimed invention is expected to provide good results.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. In a method of treating a liver-associated disease in a patient, which method includes the step of delivering an effective amount of an active compound to the desired site in the patient, said active compound being a uridine or a uracil base analog, the improvement wherein said delivering step comprises administering to the patient a prodrug having a structure corresponding to that of said active compound except that a keto group on the uracil ring structure is reduced, said prodrug being oxidized to its active diketo-containing form by human hepatic aldehyde oxidase, wherein said active compound is formed in situ in the liver of the patient by oxidation of said prodrug by means of hepatic aldehyde oxidase, said prodrug being administered in an amount sufficient to form an effective amount of said active compound upon oxidation of said prodrug by hepatic aldehyde oxidase.

2. The method of claim 1 wherein said prodrug has the formula:

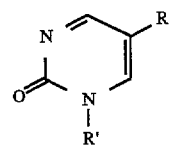

wherein R is I, F, Br, Cl, —OR$^1$, —CF$_3$, NO$_2$, SR$^1$, —CH=CR$^2$R$^3$, —C≡CR$^2$ or —N=N$^+$=N$^-$, R$^1$ is an alkyl group from 1 to 5 carbon atoms, R$^2$ and R$^3$, independently of each other, are hydrogen, a C$_1$–C$_5$-alkyl group or a halogen, and R' is hydrogen, a sugar, or an analog of a sugar.

3. The method of claim 2, wherein said active compound is a 5-substituted UdR compound and said prodrug is a corresponding 5-substituted PdR compound.

4. The method of claim 3, wherein said 5-substituent is I, F, Br, Cl, —OR$^1$, —CF$_3$, NO$_2$, SR$^1$, —CH=CR$^2$R$^3$, —C≡CR$^2$ or —N=N$^+$=N$^-$, R$^1$ being an alkyl group from 1 to 5 carbon atoms, and R$^2$ and R$^3$, independently of each other, being hydrogen, a C$_1$–C$_5$-alkyl group or a halogen.

5. The method of claim 3, wherein said active compound is IUdR and said prodrug is IPdR.

6. The method of claim 2, wherein said active compound is other than a 5-substituted UdR compound.

7. The method of claim 6, wherein said active compound is a 5-substituted uracil.

8. The method of claim 7, wherein said 5-substituent is I, F, Br, Cl, —OR$^1$, —CF$_3$, NO$_2$, SR$^1$, —CH=CR$^2$R$^3$, —C≡CR$^2$ or —N=N$^+$=N$^-$, R$^1$ being an alkyl group from 1 to 5 carbon atoms, and R$^2$ and R$^3$, independently of each other, being hydrogen, a C$_1$–C$_5$-alkyl group or a halogen.

9. The method of claim 2, wherein, in said prodrug, R' is:

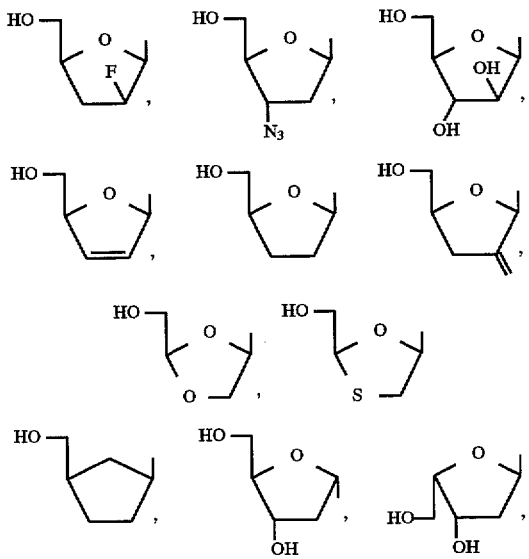

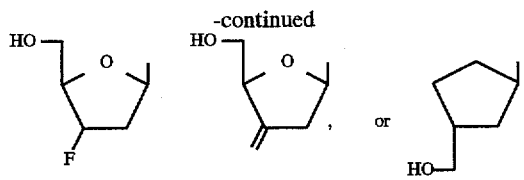
-continued

10. The method of claim 2, wherein said R' is hydrogen, a sugar, or a sugar residue.

11. The method of claim 10, wherein said R' is a ribose or deoxyribose.

12. The method of accordance with claim 2, wherein R' is hydrogen or a deoxyribose.

13. The method of claim 1, wherein said liver associated disease is hepato-carcinoma.

14. The method of claim 1, wherein said active compound is one which cannot be effectively administered orally and wherein said prodrug is administered orally.

15. In a method for the treatment of hepato-carcinoma in a patient, which method includes delivering an effective amount of a 5-substituted UdR compound to the desired site in the patient, the improvement wherein said delivery step comprises administering to the patient a corresponding 5-substituted PdR compound, whereby said 5-substituted UdR compound is formed in situ in the liver of the patient by oxidation of said 5-substituted PdR compound by means of hepatic aldehyde oxidase, wherein said 5-substituted PdR compound is administered in an amount sufficient to form said effective amount of 5-substituted UdR compound upon oxidation of said prodrug by hepatic aldehyde oxidase.

16. The method of claim 15, wherein said 5-substituent is I, F, Br, Cl, —OR$^1$, —CF$_3$, NO$_2$, SR$^1$, —CH=CR$^2$R$^3$, —C≡CR$^2$ or —N=N$^+$—N$^-$, R$^1$ being an alkyl group from 1 to 5 carbon atoms, and R$^2$ and R$^3$, independently of each other, being hydrogen, a C$_1$–C$_5$-alkyl group or a halogen.

17. In a method for the treatment of a patient having a condition which responds to treatment which includes the step of delivering an effective amount of a bio-affecting compound to a desired site in the patient, said compound being a uracil or uracil base analog and being incapable of being effectively administered orally, the improvement wherein said delivering step comprises orally administering to the patient a prodrug having a structure corresponding to that of said compound except that a keto group on the uracil ring structure is reduced, said prodrug being oxidized to said compound by human hepatic aldehyde oxidase, wherein said compound is formed in situ in the liver of the patient by oxidation of said prodrug by means of hepatic aldehyde oxidase, said prodrug being administered in an amount sufficient to form an effective amount of said compound upon oxidation of said prodrug by hepatic aldehyde oxidase.

18. The method of claim 17 wherein said prodrug has the formula:

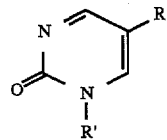

wherein R is I, F Br, Cl, H, —CH$_3$, —OR$^1$, —CF$_3$, NO$_2$, SR$^1$, —CH=CR$^2$R$^3$, —C≡CR$^2$ or —N=N$^+$=N$^-$, R$^1$ is an alkyl group from 1 to 5 carbon atoms, R$^2$ and R$^3$, independently of each other, are hydrogen, a C$_1$–C$_5$-alkyl group or a halogen, and R' is hydrogen, a sugar residue, —CH$_2$—O—CH$_2$—CH$_2$OH, —CH$_2$—O—CH(CH$_2$OH), substituted or unsubstituted alkyl, aryl, cycloalkyl, cycloaryl or any other desired residue, wherein such residue is not of such size as to sterically hinder the action of the hepatic aldehyde oxidase.

19. The method of claim 18, wherein, in said prodrug, R' is:

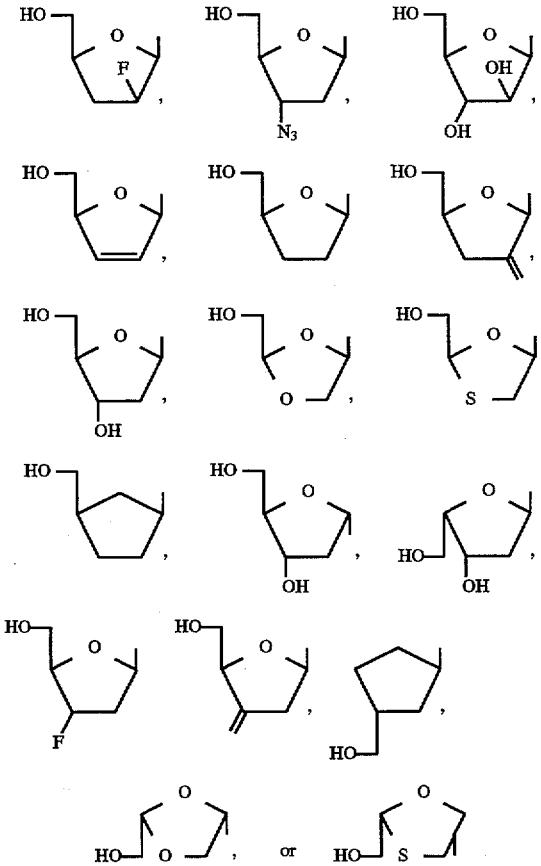

20. The method of claim 17, wherein said bio-affecting compound is a 5-substituted uracil.

21. The method of claim 20, wherein said 5-substituent is I, F, Br Cl, H, —CH$_3$, —OR$^1$, —CF$_3$, NO$_2$, SR$^1$, —CH=CR$^2$R$^3$, —C≡CR$^2$ or —N=N$^+$=N$^-$, R$^1$ being an alkyl group from 1 to 5 carbon atoms, and R$^2$ and R$^3$, independently of each other, being hydrogen, a C$_1$–C$_5$-alkyl group or a halogen.

22. The method of claim 17, wherein said prodrug is 5-fluoro-2-pyrimidinone.

23. In a method for the treatment of a patient having a condition which responds to treatment which includes the step of delivering an effective amount of a bio-affecting compound to a desired site in the patient, said compound being a uracil base analog, the improvement wherein said delivering step comprises administering to the patient a prodrug having a structure corresponding to that of said compound except that a keto group on the uracil ring structure is reduced, said prodrug being oxidized to its bio-affecting diketo-containing form by human hepatic aldehyde oxidase, wherein said active compound is formed in situ in the liver of the patient by oxidation of said prodrug by means of hepatic aldehyde oxidase, said prodrug being administered in an amount sufficient to form an effective amount of said active compound upon oxidation of said prodrug by hepatic aldehyde oxidase, wherein said prodrug has the formula

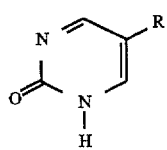
wherein R is I, F, Br, Cl, H, —$CH_3$, —$OR^1$, —$CF_3$, $NO_2$, $SR^1$, —$CH=CR^2R^3$, —$C\equiv CR^2$ or —$N=N^+-N^-$, $R^1$ is an alkyl group from 1 to 5 carbon atoms, $R^2$ and $R^3$, independently of each other, are hydrogen, a $C_1$-$C_5$-alkyl group or a halogen.
* * * * *